US009255130B2

(12) United States Patent
Yu et al.

(10) Patent No.: US 9,255,130 B2
(45) Date of Patent: Feb. 9, 2016

(54) PUF-A AND RELATED COMPOUNDS FOR TREATMENT OF RETINOPATHIES AND SIGHT-THREATENING OPHTHALMOLOGIC DISORDERS

(75) Inventors: John Yu, La Jolla, CA (US); Alice Yu, La Jolla, CA (US); Ming-Wei Kuo, Sanchong (TW); Jui-Chin Chang, Taipei (TW)

(73) Assignee: Academia Sinica, Taipei (TW)

( * ) Notice: Subject to any disclaimer, the term of this patent is extended or adjusted under 35 U.S.C. 154(b) by 672 days.

(21) Appl. No.: 13/056,975

(22) PCT Filed: Jul. 29, 2009

(86) PCT No.: PCT/US2009/004373
§ 371 (c)(1), (2), (4) Date: Apr. 28, 2011

(87) PCT Pub. No.: WO2010/014218
PCT Pub. Date: Feb. 4, 2010

(65) Prior Publication Data

US 2013/0202678 A1 Aug. 8, 2013

Related U.S. Application Data

(60) Provisional application No. 61/137,427, filed on Jul. 29, 2008.

(51) Int. Cl.

| | |
|---|---|
| ***A61K 48/00*** | (2006.01) |
| ***C07K 14/47*** | (2006.01) |
| ***C07K 16/18*** | (2006.01) |
| ***C12N 15/113*** | (2010.01) |
| ***C12Q 1/68*** | (2006.01) |
| ***G01N 33/68*** | (2006.01) |

(52) U.S. Cl.
CPC .......... *C07K 14/4747* (2013.01); *A61K 48/005* (2013.01); *C07K 16/18* (2013.01); *C12N 15/113* (2013.01); *C12Q 1/6876* (2013.01); *G01N 33/6854* (2013.01); *C12N 2799/025* (2013.01)

(58) Field of Classification Search
None
See application file for complete search history.

(56) References Cited

PUBLICATIONS

Rossmiller et al. Mole Vision 2012;18:2479-96.*
Kuo et al. PloS One 2009;4:e4980,1-12.*
Fan et al. Tumor Biol 2013;34:2557-64, the abstract.*

* cited by examiner

*Primary Examiner* — Janice Li
(74) *Attorney, Agent, or Firm* — Shantanu Basu; Eckman Basu LLP

(57) ABSTRACT

Methods and compositions for treating retinal diseases comprising therapeutic amounts of a compound selected from a normal Puf-A gene product, an active polypeptide fragment thereof, an analog thereof or a peptidomimetic thereof. Vectors, including AAV vectors comprising the therapeutic compound are provided. Puf-A compositions suitable for subretinal, intravitreal, topical, subconjunctival, retrobulbar, periocular, suprachoroidal, or intraocular administration are provided. Methods for screening siRNA, RNAi and shRNA, small molecules and monoclonal antibodies that inhibit Puf-A target activity and reduce apoptosis are provided.

18 Claims, 8 Drawing Sheets

```
ccgtaaagttgtttgtctgtacacatggtccatt   34

ATGGAGGGTAAACCAAGAAAGAAATCATTCACTCCAAGAGACGGAAAGAAACCTTCATTCAAATCCAAAGGTAAACCTGGAGGAAAACCA   124
 M  E  G  K  P  R  K  K  S  F  T  P  R  D  G  K  K  P  S  F  K  S  K  G  K  P  G  G  K  P   30
CAAGGCAAACGGCCATTCAAACCTCACAACAATGACAAAGGCAAAGGTTTTAGAAAGTCAGGTGGAGAAGGAGGACCACAGAAGTTCAAC   214
 Q  G  K  R  P  F  K  P  H  N  N  D  K  G  K  G  F  R  K  S  G  G  E  G  G  P  Q  K  F  N   60
AGAAAACCAACAGATGGAAAATTTGCCAAGAAGAGAAAATTTCCTGGAGACAGAATCAAACAAGAGGAAGGTGCTGAGCGAAAAAAACCT   304
 R  K  P  T  D  G  K  F  A  K  K  R  K  F  P  G  D  R  I  K  Q  E  E  G  A  E  R  K  K  P   90
AAATGGGATGAGTTTAAACAAAAAAAGAAAGAACTGAAGCTGAATCGTCAGCAGACTGATAGAAAAGAGAGCTACCAGATCGTAAGCAGA   394
 K  W  D  E  F  K  Q  K  K  K  E  L  K  L  N  R  Q  Q  T  D  R  K  E  S  Y  Q  I  V  S  R   120
GCAAAGCAAGTGTGGGAGATGGTAAGACGGAAAGACTGTGATAAGCAAAAAAGGACTAAACTGATGAAAGAGCTGCAGGATCTTGTAAAA   484
 A  K  Q  V  W  E  M  V  R  R  K  D  C  D  K  Q  K  R  T  K  L  M  K  E  L  Q  D  L  V  K   150
GGCAAAATTAAAACGATTGCATTTGCGCATGATTCCACGCGGGTGCTTCAGTGTTTTATTCAATTTGGCAGTGATAAGCAGAGAAAGGAG   574
 G  K  I  K  T  I  A  F  A  H  D  S  T  R  V  L  Q  C  F  I  Q  F  G  S  D  K  Q  R  K  E   180
GTGTTTGATGAACTCAAAGAACACATTGTGGAGTTGAGTAAATCAAAATATGCCAGAAACATTGTAAAGAAGTTCCTAATGTATGGGAGT   664
 V  F  D  E  L  K  E  H  I  V  E  L  S  K  S  K  Y  A  R  N  I  V  K  K  F  L  M  Y  G  S   210
AAAGAGCAGGTAGGTGAAGTGATGTTGGCTTTTAAAGGGAAAGTCAGGCAGATGCTCAGACACTCGGAGGCGTCTTCAGTTGTGGAATAC   754
 K  E  Q  V  G  E  V  M  L  A  F  K  G  K  V  R  Q  M  L  R  H  S  E  A  S  S  V  V  E  Y   240
GCTTATAATGATAAAGCCATCCTCTCTCAGAGACTCATGCTCACTGAGGAGCTCTACGGAAACACGTTCACCGTCTTAAAGTCATCAGTT   844
 A  Y  N  D  K  A  I  L  S  Q  R  L  M  L  T  E  E  L  Y  G  N  T  F  T  V  L  K  S  S  V   270
TGTCCTACGTTAGAGAAAGTTCTTGAAGCAAATCCAGGGAAATTGGAGAGCATCTTGGATGAAATGAAGCAGATCCTTACACCCATGGCA   934
 C  P  T  L  E  K  V  L  E  A  N  P  G  K  L  E  S  I  L  D  E  M  K  Q  I  L  T  P  M  A   300
CAGAAAGAGGCTGTCATTAAACATTCATTGGTTCACAAAGTTTTCCTGGACTTCTTTGAGCACGCTCCGGACAAACAGAGAACGGAGATG   1024
 Q  K  E  A  V  I  K  H  S  L  V  H  K  V  F  L  D  F  F  E  H  A  P  D  K  Q  R  T  E  M   330
ATTGAGTCGATCAGAGAGGCCGTCGTGTACATGGCACACACACACGATGGAGCCAGAGTCACCATGCACTGTTTATGGCACGGCACAACT   1114
 I  E  S  I  R  E  A  V  V  Y  M  A  H  T  H  D  G  A  R  V  T  M  H  C  L  W  H  G  T  T   360
AAGGACCGAAAGGTTATAGTAAAAACGATGAAATCGTATATTGCAAAGTTTGCCATGGGTGAATATGCTCATCTTGTACTTTTGGCTGCA   1204
 K  D  R  K  V  I  V  K  T  M  K  S  Y  I  A  K  F  A  M  G  E  Y  A  H  L  V  L  L  A  A   390
TTCGATTGCATTGATGACACCAAGCTGGTTAAACAAATTATTATCTCAGAAATGGTTAGTTCCTTATCTGAAATAATCAGCAATAAACAC   1294
 F  D  C  I  D  D  T  K  L  V  K  Q  I  I  I  S  E  M  V  S  S  L  S  E  I  I  S  N  K  H   420
GGTAAAAAGGTGCTGCTTTACCTGCTGAGTCCTAGAGACCCTGCTCACCTCTTACCTGAAATCATTCAAGTGCTGGAGAAAGGGGATGGC   1384
 G  K  K  V  L  L  Y  L  L  S  P  R  D  P  A  H  L  L  P  E  I  I  Q  V  L  E  K  G  D  G   450
AATGCGCACAGTAAGAAGGATGTGCTGATCAGGAGAAAGGAGCTGCTGGAGGCCGCGTCTCCTTCTCTGCTGAATCATCTGTGTGAAAAC   1474
 N  A  H  S  K  K  D  V  L  I  R  R  K  E  L  L  E  A  A  S  P  S  L  L  N  H  L  C  E  N   480
GCTCAGTCTATGGTCATGGATAAATCCTGCTGTGTGGTGGTGAGCGACATACTGGGCTCTGCTGTTGGAGATCTCAGACCTGCTATGGAG   1564
 A  Q  S  M  V  M  D  K  S  C  C  V  V  V  S  D  I  L  G  S  A  V  G  D  L  R  P  A  M  E   510
GCAGTGGCAGCTCTGGCAGATGGACCCCTTATACCAGGTGGAAAGGATGGACAGCTGCATATGGCTGAACACCCCGCTGGTCATCTGGTG   1654
 A  V  A  A  L  A  D  G  P  L  I  P  G  G  K  D  G  Q  L  H  M  A  E  H  P  A  G  H  L  V   540
CTGAAATGGTTGATCGAGCAGGACACCAAGATGAAGGACACAGAGAGAGAGGAGCGTTTTTCCAGGATTCTTCTGGAGAAGGTTGGGTTG   1744
 L  K  W  L  I  E  Q  D  T  K  M  K  D  T  E  R  E  E  R  F  S  R  I  L  L  E  K  V  G  L   570
GAGAACCTCAAGACATGGGCTTCGGTCAACCGTGGTGCCATTATTCTTTGTTGTCTTCTCCAGAGCGCAGATGAAAGTGTTGCTGAAGAA   1834
 E  N  L  K  T  W  A  S  V  N  R  G  A  I  I  L  C  C  L  L  Q  S  A  D  E  S  V  A  E  E   600
GTGAAAGCTATGCTGAAATCCAGCATTCCTGAGCTACAGCGGCTCCAGAACTCAAAAGGAATTGAGGTTCTGCTTGAAAAACTTGCATAA   1924
 V  K  A  M  L  K  S  S  I  P  E  L  Q  R  L  Q  N  S  K  G  I  E  V  L  L  E  K  L  A  *   630
aaagttcgatctatcaatgatttttctttgttttctccagtttttttaaaattgtgcatttctatgatgttgtatgtaaatacaaattac   2014

acacaatgagacctggaaaaaaaaaaaaaaaaaaaaa   2053
```

Figure 1

```
  1 GGCCCGGGGGCGGAGCAAGGCAAGGAAGCGGAAGCGGAGAGGCGG
    TCGGGATCCGCTGCGCGAGCTGTCTCGGTCCCACGTGTGCGAGTT
    GCTACG

 97 ATGGAAGTTAAAGGGAAAAAGCAATTCACAGGAAAGAGTACAAAG
    M  E  V  K  G  K  K  Q  F  T  G  K  S  T  K     15
142 ACAGCACAAGAAAAAAACAGATTTCATAAAAATAGTGATTCTGGT
    T  A  Q  E  K  N  R  F  H  K  N  S  D  S  G     30
187 TCTTCAAAGACATTTCCAACAAGGAAAGTTGCTAAAGAAGGTGGA
    S  S  K  T  F  P  T  R  K  V  A  K  E  G  G     45
232 CCTAAAGTCACATCTAGGAACTTTGAGAAAAGTATCACAAAACTT
    P  K  V  T  S  R  N  F  E  K  S  I  T  K  L     60
277 GGGAAAAAGGGTGTAAAGCAGTTCAAGAATAAGCAGCAAGGGGAC
    G  K  K  G  V  K  Q  F  K  N  K  Q  Q  G  D     75
322 AAATCACCAAAGAACAAATTCCAGCCGGCAAATAAATTCAACAAG
    K  S  P  K  N  K  F  Q  P  A  N  K  F  N  K     90
367 AAGAGAAAATTCCAGCCAGATGGTAGAAGCGATGAATCAGCAGCC
    K  R  K  F  Q  P  D  G  R  S  D  E  S  A  A    105
412 AAGAAGCCCAAATGGGATGACTTCAAAAAGAAGAAGAAAGAACTG
    K  K  P  K  W  D  D  F  K  K  K  K  K  E  L    120
457 AAGCAAAGCAGACAACTCAGTGATAAAACCAACTATGACATTGTT
    K  Q  S  R  Q  L  S  D  K  T  N  Y  D  I  V    135
502 GTTCGGGCAAAGCAGATGTGGGAGATTTTAAGAAGAAAAGACTGT
    V  R  A  K  Q  M  W  E  I  L  R  R  K  D  C    150
547 GACAAAGAAAAAAGAGTAAAGTTAATGAGTGATTTGCAGAAGTTG
    D  K  E  K  R  V  K  L  M  S  D  L  Q  K [L]   165
592 ATTCAAGGGAAAATTAAAACTATTGCATTTGCACACGATTCAACT
   [I  Q  G  K  I  K  T  I  A  F  A  H  D  S  T]   180
637 CGTGTGATCCAGTGTTACATTCAGTATGGTAATGAAGAACAGAGA
   [R  V  I  Q  C  Y  I  Q  Y  G  N  E  E  Q  R]   195
682 AAACAGGCTTTTGAAGAATTGCGAGATGATTTGGTTGAGTTAAGT
   [K  Q  A  F  E  E  L  R  D  D  L  V  E  L  S]   210
727 AAAGCCAAATATTCGAGAAATATTGTTAAGAAATTTCTCATGTAT
   [K  A  K  Y  S  R  N  I  V  K  K  F  L  M  Y]   225
772 GGAAGTAAACCACAGATTGCAGAGATAATCAGAAGTTTTAAAGGC
   [G  S  K  P  Q  I  A  E  I  I  R  S  F  K  G]   240
817 CACGTGAGGAAGATGCTGCGGCATGCGGAAGCATCAGCCATCGTG
   [H  V  R  K  M  L  R  H  A  E  A  S  A  I  V]   255
862 GAGTACGCATACAATGACAAAGCCATTTTGGAGCAGAGGAACATG
   [E  Y  A  Y  N  D  K  A  I  L  E  Q  R  N  M]   270
907 CTGACGGAAGAGCTCTATGGGAACACATTTCAGCTTTACAAGTCA
   [L  T  E  E  L  Y  G  N  T  F  Q  L  Y  K  S]   285
952 GCAGATCACCGAACTCTGGACAAAGTGTTAGAGGTACAGCCAGAA
   [A  D  H  R  T  L  D  K  V  L  E  V  Q  P  E]   300
```

Figure 2A

```
 997 AAATTAGAACTTATTATGGATGAAATGAAACAGATTCTAACTCCA
     K  L  E  L  I  M  D  E  M  K  Q  I  L  T  P   315
1042 ATGGCCCAAAAGGAAGCTGTGATTAAGCACTCATTGGTGCATAAA
     M  A  Q  K  E  A  V  I  K  H  S  L  V  H  K   330
1087 GTATTCTTGGACTTTTTTACCTATGCACCCCCCAAACTCAGATCA
     V  F  L  D  F  F  T  Y  A  P  P  K  L  R  S   345
1132 GAAATGATTGAAGCCATCCGCGAAGCGGTGGTCTACCTGGCACAC
     E  M  I  E  A  I  R  E  A  V  V  Y  L  A  H   360
1177 ACACACGATGGCGCCAGAGTGGCCATGCACTGCCTGTGGCATGGC
     T  H  D  G  A  R  V  A  M  H  C  L  W  H  G   375
1222 ACGCCCAAGGACAGGAAAGTGATTGTGAAAACAATGAAGACTTAT
     T  P  K  D  R  K  V  I  V  K  T  M  K  T  Y   390
1267 GTTGAAAAGGTGGCTAATGGCCAATACTCCCATTTGGTTTTACTG
     V  E  K  V  A  N  G  Q  Y  S  H  L  V  L  L   405
1312 GCGGCATTTGATTGTATTGATGATACTAAGCTTGTGAAGCAGATA
     A  A  F  D  C  I  D  D  T  K  L  V  K  Q  I   420
1357 ATCATATCAGAAATTATCAGTTCATTGCCTAGCATAGTAAATGAC
     I  I  S  E  I  I  S  S  L  P  S  I  V  N  D   435
1402 AAATATGGAAGGAAGGTCCTATTGTACTTACTAAGCCCCAGAGAT
     K  Y  G  R  K  V  L  L  Y  L  L  S  P  R  D   450
1447 CCTGCACATACAGTACGAGAAATCATTGAAGTTCTGCAAAAAGGA
     P  A  H  T  V  R  E  I  I  E  V  L  Q  K  G   465
1492 GATGGAAATGCACACAGTAAGAAAGATACAGAGGTCCGCAGACGG
     D  G  N  A  H  S  K  K  D  T  E  V  R  R  R   480
1537 GAGCTCCTAGAATCCATTTCTCCAGCTTTGTTAAGCTACCTGCAA
     E  L  L  E  S  I  S  P  A  L  L  S  Y  L  Q   495
1582 GAACACGCCCAAGAAGTGGTGCTAGATAAGTCTGCGTGTGTGTTG
     E  H  A  Q  E  V  V  L  D  K  S  A  C  V  L   510
1627 GTGTCTGACATTCTGGGATCTGCCACTGGAGACGTTCAGCCTACC
     V  S  D  I  L  G  S  A  T  G  D  V  Q  P  T   525
1672 ATGAATGCCATCGCCAGCTTGGCAGCAACAGGACTGCATCCTGGT
     M  N  A  I  A  S  L  A  A  T  G  L  H  P  G   540
1717 GGCAAGGACGGAGAGCTTCACATTGCAGAACATCCTGCAGGACAT
     G  K  D  G  E  L  H  I  A  E  H  P  A  G  H   555
1762 CTAGTTCTGAAGTGGTTAATAGAGCAAGATAAAAAGATGAAAGAA
     L  V  L  K  W  L  I  E  Q  D  K  K  M  K  E   570
1807 AATGGGAGAGAAGGTTGTTTTGCAAAAACACTTGTAGAGCATGTT
     N  G  R  E  G  C  F  A  K  T  L  V  E  H  V   585
1852 GGTATGAAGAACCTGAAGTCCTGGGCTAGTGTAAATCGAGGTGCC
     G  M  K  N  L  K  S  W  A  S  V  N  R  G  A   600
1897 ATTATTCTTTCTAGCCTCCTCCAGAGTTGTGACCTGGAAGTTGCA
     I  I  L  S  S  L  L  Q  S  C  D  L  E  V  A   615
```

Figure 2B

```
1942 AACAAAGTCAAAGCTGCACTGAAAAGCTTGATTCCTACATTGGAA
     N  K  V  K  A  A  L  K  S  L  I  P  T  L  E   630
1987 AAAACCAAAAGCACCAGCAAAGGAATAGAAATTCTACTTGAAAAA
     K  T  K  S  T  S  K  G  I  E  I  L  L  E  K   645
2032 CTGAGCACATAG
     L  S  T  *   648 (SEQ ID NO: 2)

2044 GTGGAAAGAGTTAAGAGCAAGATGGAATGATTTTTTCTGTTCTCT
     GTTCTGTTTCCCAATGCAGAAAAGAAGGGGTAGGGTCCACCATAC
     TGGTAATTGGGGTACTCTGTATATGTGTTTCTTCTTTGTATACGA
     ATCTATTTATATAAATTGTTTTTTAAATGGTCTTTTTTAAAAAA
2224 AAAAAAAAA 2232    (SEQ ID NO: 1)
```

PUF-A AND RELATED COMPOUNDS FOR TREATMENT OF RETINOPATHIES AND SIGHT-THREATENING OPHTHALMOLOGIC DISORDERS

CROSS-REFERENCE TO RELATED APPLICATIONS

This application is a US National Stage Entry under §371 of international application PCT/US2009/004373 titled "Puf-A and related compounds for treatment of Retinopathies and sight-threatening ophthalmologic disorders" filed Jul. 29, 2009. This application claims priority of provisional patent application U.S. Ser. No. 61/137,427, titled "Identification of Biological functions of novel genes in Zebrafish through Predictive Evolutionary Analysis: Characterization of Puf-A Gene and Associated Protein With Functions Involved In the Development of Eyes and Primordial Germ Cells" filed Jul. 29, 2008, the contents of which are incorporated herein in their entirety by reference.

REFERENCE TO SEQUENCE LISTING

Pursuant to 37 C.F.R. 1.821(c), a sequence listing was submitted as an ASCII compliant text file named "SEQ_Listing_ST25.txt" that was created on Dec. 14, 2009 and has a size of 17,150 bytes. The content of the aforementioned file "SEQ_Listing_ST25.txt" is hereby incorporated by reference in its entirety.

TECHNICAL FIELD OF THE INVENTION

The present invention relates to methods for the treatment of retinopathies and various sight-losing disorders. In particular, the invention relates to the Puf-A gene product and related compounds, mimetics and related compounds for the treatment of eye-related disorders.

BACKGROUND OF THE INVENTION

The primary concern of ophthalmologists for age-related retinopathies and various sight-losing disorders is preserving the sight of patients. For example, open angle glaucoma, Leber's hereditary optic neuropathy, age-related macular degeneration, diabetic retinopathy, retinal ischemia, and a variety of retinitis pigmentosa. It has been known that various retinopathies and age-related ophthalmologic disorders lead to a progressive loss of vision.

Most often, these eye diseases are characterized by a gradual degeneration of retinal ganglion cells and eventual loss of the photoreceptors in the retina. (Quigley, H. A. 1999. Neuronal death in glaucoma. Prog. Retin. Eye Res. 18:39-57.) Cell death occurs through the process of apoptosis. Ischemic proliferative retinopathy (e.g., diabetes mellitus, retinopathy of prematurity, or retinal vein occlusion) is a major cause of blindness worldwide. Apart from neovascularization, ischemic proliferative retinopathy leads to retinal degeneration. Apoptosis has been ascribed to be the leading mechanism in ischemic retinal degeneration. (Adamis A P, Aiello L P, D'Amato R A (1999) Angiogenesis and ophthalmic disease. Angiogenesis 3:9-14). Apoptosis also is involved in age-related macular degeneration. (Hinton D M et al., Arch. Ophthalmol., 116:203-209 (1998). However, at the present time, there is no cure for these age-related eye diseases and blindness.

Glaucoma, an optic neuropathy affecting nearly 60 million people, is the second leading cause of blindness worldwide. (Quigley H A, Broman A T (2006) The number of people with glaucoma worldwide in 2010 and 2020. Br J Ophthalmol 90:262-267). Visual field changes in glaucoma are believed to be caused by the loss of retinal ganglion cells (RGCs), although the exact cause of RGC degeneration is still unknown (Kuehn M H, Fingert J H, Kwon Y H (2007) Retinal ganglion cell death in glaucoma: mechanisms and neuroprotective strategies. Ophthalmol Clin North Am 18:383-395).

A novel gene, designated as puf-A, was cloned and functionally characterized, and its homologs in zebrafish, mouse, and human were identified as one of the three homolog clusters which were consisted of 14 related proteins with Puf repeats. Computer modeling of human Puf-A structure and a pull-down assay for interactions with RNA targets predicted that it was a RNA-binding protein. Knockdown of puf-A in zebrafish embryos resulted in microphthalmia, a small head, and abnormal primordial germ-cell migration. (Kuo M-W et al., A Novel puf-A Gene Predicted from Evolutionary Analysis Is Involved in the Development of Eyes and Primordial Germ-Cells. PLoS ONE 4(3): e4980. (2009)).

The Puf family is an evolutionarily conserved protein family named after Pumilio (*Drosophila*) and FBF (Fem-3 mRNA-binding Factor, *Caenorhabditis elegans*). Puf proteins have been found in various organisms, including yeast, *C. elegans, Drosophila*, zebrafish, *Xenopus*, mouse, and human, but their function is largely unclear. The first Puf protein, Pumilio, identified from *Drosophila*, was known to repress translation of hunchback mRNA in the posterior half of the *Drosophila* embryo, thereby permitting abdominal development. (Murata Y, Wharton R P (1995) Binding of pumilio to maternal hunchback mRNA is required for posterior patterning in *Drosophila* embryos. Cell 80:747-756.) In addition to its role in posterior patterning of embryos, *Drosophila* Pumilio functions in the development of germline stem cells. (Braat A K, Zandbergen T, van de Water S, Goos H J, Zivkovic D (1999) Characterization of zebrafish primordial germ cells: morphology and early distribution of vasa RNA. Dev Dyn 216: 153-167). Puf family members are usually identified by the presence of eight tandem Puf repeats of ~35-39 amino acids (Wang X, McLachlan J, Zamore P D, Hall T M (2002) Modular recognition of RNA by a human pumilio-homology domain. Cell 110: 501-512.) and the repeat binds to specific sequences in the 39 untranslated region (UTR) of a target mRNA.

The novel puf-A gene is involved in eye and primordial germ-cell (PGC) development. Analysis using the SMART server identified 14 puf-A related proteins in human, mouse and zebrafish. A computer modeling of human Puf-A predicted that it is a unique RNA-binding protein composed of six Puf repeats. (Kuo et al., PLoS ONE 4(3): e4980. (2009)). Computer modeling of human Puf-A structure and a pull-down assay for interactions with RNA targets predicted that it was a RNA-binding protein. Specifically, Puf-A contained a special six Puf-repeat domain, which constituted a unique superhelix half doughnut-shaped Puf domain with a topology similar to, but different from the conventional eight-repeat Pumilio domain. In mice, puf-A expression was detected primarily in retinal ganglion and pigmented cells of eye tissues. In some exemplary implementations is a unique puf-A gene that was shown to play a role in the development of eyes. The Puf-A protein, encoded by the unique puf-A gene, is expressed prominently in retinal ganglion cells. The expressed Puf-A protein has anti-apoptotic functions.

In zebrafish, the formation of retinal neurons follows a phylogenetically conserved order during embryogenesis. All six retinal neuron types are generated from common multipotent progenitors, with retinal ganglion cells being the first neurons to occur. Morphants of 3- and 5-days post fertilization (dpf embryos) have been shown to have incomplete differentiation patterns in the retina, thus indicating that the Puf-A protein plays a role in the development of retinal progenitors.

Additionally, during embryonic development, knockdown of the puf-A gene has led to a reduction in the number of PGCs and their abnormal migration. These results show that Puf-A is involved in the maintenance and migration of these primitive germ cells. The expression of puf-A was found predominantly in stage I follicles in adult ovaries and became undetectable in stage II and III follicles during subsequent oocyte development. It was noted that the most primitive germline stem cells, oogonia, were not readily distinguishable from stage I follicles. Thus, indicating that Puf-A not only regulates primordial germ cells (PGCs) development but may also play a role in germline stem cells up to stage I follicles. It is noteworthy that progressive ganglion cell degeneration precedes neuronal loss in many eye diseases.

SUMMARY OF THE INVENTION

Because the newly found human gene, Puf-A, is expressed in retinal ganglion and pigmented cells of eye tissues and displays a unique anti-apoptotic activity, Puf-A genes and related derivatives serve as targets for developing new therapeutic products for age-related and sight-threatening eye diseases.

Since the novel puf-A gene plays an important role in eye development, for example in the development of retinal progenitors and the regulation of PGC development, the gene and/or its products can be used for anti-apoptotic effects for the treatment of disease states including but not limited to progressive ganglion cell degeneration, retinitis pigmentosa, retinal ischemia, and glaucoma. This novel gene is an inhibitor of apoptosis, especially of caspase 3, and overexpression may thus lead to neuronal protection for retinal cells due to its anti-apoptotic activity.

Puf-A gene possessing anti-apoptotic actions is primarily expressed in retinal ganglion cells (GC) and retinal pigmented epithelial cells (RPE). Since many sight-threatening diseases including open angle glaucoma, Leber's hereditary optic neuropathy, age-related macular degeneration, diabetic retinopathy, and a variety of retinitis pigmentosa are caused by progressive neuronal apoptosis, intraocular delivery of Puf-A gene and related Puf-A gene and related truncated fragment sequences or chemical compounds would be the choice of future therapies for those who suffer or will suffer from blindness. The invention relates to intraocular delivery of Puf-A gene and related truncated fragment sequences or chemical compounds may offer neuronal protection for retinal cells due to this specific anti-apoptotic activity.

The invention further relates local delivery (by injection or other means) of adeno-associated virus (AAV) encoding Puf-A and/or its truncated derivatives into the sub-retinal or intravitreal space in the eye, and infect ganglion and photoreceptor cells with high efficiency.

Alternatively, the invention relates to chemical compounds and small molecule mimetics to either enhance the expression of Puf-A or affect its downstream targets (e.g. HtrA2), thereby preventing retinal apoptosis.

In one aspect, the invention provides a method for treating an ocular disorder in a human or animal subject characterized by the defect or absence of a normal gene in the ocular cells. The method includes administering to the subject by subretinal or intravitreal injection an effective amount of a recombinant adeno-associated virus (AAV) carrying a nucleic acid sequence encoding the normal Puf-A gene, an active polypeptide fragment thereof, an analog thereof or a peptidomimetic thereof, under the control of a promoter sequence which expresses the product of the gene in the ocular cells. In some embodiments the AAV vector infects ganglion and photoreceptor cells with high efficiency.

In another aspect, the invention provides a method for treating an ocular disorder in a human or animal subject by administering to the subject by subretinal, intravitreal, topical, subconjunctival, retrobulbar, periocular, suprachoroidal, or intraocular injection an effective amount of a recombinant vector carrying a nucleic acid sequence encoding a normal Puf-A gene, an active polypeptide fragment thereof, an analog thereof or a peptidomimetic thereof, under the control of a promoter sequence which expresses the product of the gene in the ocular cells. In one embodiment, the promoters are cell-specific promoters.

In another aspect, expression of the normal Puf-A gene, an active polypeptide fragment thereof, an analog thereof or a peptidomimetic thereof in an ocular cell of a subject, provides to the cells the product necessary to restore or maintain vision in the subject.

In another embodiment, the invention provides a composition for treatment of an ocular disorder characterized by the defect or absence of a normal gene in the ocular cells of the subject. Such compositions comprise effective amounts of a recombinant adeno-associated virus carrying a nucleic acid sequence encoding the normal Puf-A gene, an active polypeptide fragment thereof, an analog thereof or a peptidomimetic thereof, under the control of a promoter sequence which expresses the product of the gene in the ocular cells.

In one aspect, the invention provides a pharmaceutical composition for treating a retinal disorder comprising: an effective amount of an adeno-associated viral vector comprising a nucleic acid sequence suitable for expression of at least a portion of a gene encoding a therapeutic Puf-A gene product, an active polypeptide fragment thereof, an analog thereof or a peptidomimetic thereof, under the control of a promoter sequence in a desired region of the eye; and a pharmaceutically acceptable carrier.

An effective amount of an AAV vector comprises $1\times10^9$ to $2\times10^{12}$ rAAV infectious units in a volume of between 150 to 800 μl. In some embodiments the AAV vectors comprises one or more of: a promoter, a 5' regulatory element operably linked to said Puf-A nucleic acid segment; a 3' regulatory element operably linked to said nucleic acid segment; and one or more AAV-ITRs flanking said Puf-A nucleic acid segment. In some embodiments, the present invention employs a viral promoter. Suitable viral promoters are known in the art and include, for instance, cytomegalovirus (CMV) promoters, such as the CMV immediate-early promoter, promoters derived from human immunodeficiency virus (HIV), such as the HIV long terminal repeat promoter, HSV promoters, such as the Lap2 promoter or the herpes thymidine kinase promoter (Wagner et al., Proc. Natl. Acad. Sci., 78, 144-145 (1981)), promoters derived from Epstein Barr virus, an adeno-associated viral promoter, such as the p5 promoter, and the like.

The invention further provides a virion or viral particle comprising the adeno-associated viral vector of the invention. The invention further provides a mammalian host cell comprising a adeno-associated viral vector or a virion or viral particle of the invention. The mammalian host cell may be an eye cell, a scleral cell, a choroidal cell, or a retinal cell.

The invention further provides a pharmaceutical composition for treating a retinal disorder selected from the group consisting of progressive ganglion cell degeneration, retinitis pigmentosa, retinal ischemia, Leber's hereditary optic neuropathy, age-related macular degeneration, diabetic retinopathy, open angle glaucoma, and glaucoma, the composition comprising: an effective amount a normal Puf-A gene product, an active polypeptide fragment thereof, an analog thereof or a peptidomimetic thereof, a therapeutic; and a pharmaceutically acceptable carrier.

The pharmaceutical composition of the invention is suitable for delivery to a mammal by ocular injection, intravitreolar injection, retinal injection, or subretinal injection.

In some aspects, the pharmaceutical composition of the invention is suitable for delivery to a mammal systemically, or by direct or indirect administration to an ocular cell, tissue, or organ of said mammal.

In one aspect, the invention provides a method for identifying targets for anti-apoptotic therapy in ocular cells, by identifying cellular RNA bound by the Puf-A protein, and fragments, analogs and peptidomimetics thereof. RNA targets for Puf-A may be identified by any number of methods that detect RNA-protein binding including but not limited to co-immunoprecipitation, microarray analysis and the like.

In one aspect, a puf-A target of the invention comprises the products of one or more genes selected from the group consisting of zgc:193933, prdm1a, spata2, tex10, rbb4, ddx3, zp2.2, Blimp-1 and HtrA2.

In one aspect, one or more of zgc:193933, prdm1a, spata2, tex10, rbb4, ddx3, zp2.2, Blimp-1 and HtrA2 RNA is the binding target of Puf-A and the invention provides a cell-based assay to screen for effective small molecules that inhibit one or more of zgc:193933, prdm1a, spata2, tex10, rbb4, ddx3, zp2.2, Blimp-1 and HtrA2 activity and have an anti-apoptotic therapeutic effect. In one embodiment, the HtrA2 RNA is the binding target of Puf-A and the invention provides a cell-based assay to screen for effective small molecules that inhibit HtrA2 activity and have an anti-apoptotic therapeutic effect. In one embodiment, small molecules identified by these methods are useful for the treatment of human retinal diseases.

In one aspect, the invention comprises a small molecule that inhibits a Puf-A target. In one aspect, the target of the small molecule is selected from the group consisting of zgc:193933, prdm1a, spata2, tex10, rbb4, ddx3, zp2.2, Blimp-1 and HtrA2. In one embodiment the small molecule target is HtrA2.

In one aspect, the invention comprises a polynucleotide sequence that functions as at least one of a shRNA, a siRNA and a RNAi to decrease expression of a Puf-A target and reduce apoptosis. In one aspect, the target of the shRNA, a siRNA and a RNAi is selected from the group consisting of zgc:193933, prdm1a, spata2, tex10, rbb4, ddx3, zp2.2, Blimp-1 and HtrA2. In one embodiment the shRNA, a siRNA and a RNAi target is HtrA2.

The invention provides a method for treating a retinal disease, the method comprising: providing a polynucleotide sequence that functions as at least one of a shRNA, a siRNA and a RNAi suitable for reducing expression to therapeutically effective levels, a cellular RNA target bound by the Puf-A protein, fragments, analogs and peptidomimetics thereof; incorporating the polynucleotide sequence into a vector; transfecting the vector into at least one cell in a retina; and expressing a therapeutically effective amount of polynucleotide sequence to treat the retinal disease.

In one aspect, expressing the therapeutically effective amount of polynucleotide sequence generates at least one of a shRNA, a siRNA and a RNAi. In one embodiment, the vector is an AAV vector. In some embodiments, the polynucleotide sequence which generates at least one of a shRNA, a siRNA and a RNAi, comprises a sequence of the Puf-A gene. In one embodiment, expressing a therapeutically effective amount of the shRNA, siRNA or RNAi reduces apoptosis.

In one aspect, the invention comprises an antibody that functions to decrease expression of a Puf-A target and reduce apoptosis. In one aspect, the target of the antibody is selected from the group consisting of zgc:193933, prdm1a, spata2, tex10, rbb4, ddx3, zp2.2, Blimp-1 and HtrA2. In one embodiment the antibody target is HtrA2. In some embodiments the antibody is a monoclonal antibody. In some embodiments the antibody is a humanized antibody. In one aspect, the invention provides a pharmaceutical composition comprising a therapeutically effective amount of a monoclonal and/or humanized antibody according to the invention, wherein the composition is effective in reducing a retinal disorder.

In one aspect the retinal disease is selected from human retina-related degenerative disorders, including age-related glaucoma, macular degeneration, diabetic retinopathy, etc. In one aspect the retinal disease is selected from the group consisting of progressive ganglion cell degeneration, retinitis pigmentosa, retinal ischemia, Leber's hereditary optic neuropathy, age-related macular degeneration, diabetic retinopathy, open angle glaucoma, and glaucoma.

In another aspect, the invention provides a vector comprising an isolated nucleic acid comprising a nucleotide sequence encoding an amino acid sequence of human PufA recited in FIGS. 2A to 2C. In one embodiment, the vector is a viral vector selected from the group consisting of adeno-associated viral vector, herpes viral vector, parvoviral vector, and lentiviral vector. In a particular embodiment, the viral vector is an adeno-associated viral vector.

In another aspect, the invention provides a method for providing genetic therapy for treating a retinal disease, wherein an effective amount of a vector comprising an isolated nucleic acid comprising a nucleotide sequence encoding an amino acid sequence recited in FIGS. 2A to 2C is administered to a person in need of such treatment. In certain aspects, the method includes transfecting human cells with the vector. In another aspect, the method includes transfecting human ocular cells or retinal progenitor cells with the vector.

In another aspect, the invention provides an isolated peptide comprising at least 3 contiguous amino acids recited in FIGS. 2A-2C. In certain embodiments, the peptide comprises at least 3, 6, 9, 12, 15, 20, 25, 30, 35, 40, 45, 50, 55, 60, 70, 80, 90, 100 or more contiguous amino acids recited in FIGS. 2A-2C.

In another aspect, the invention provides an antibody that binds to an isolated peptide comprising at least 3 contiguous amino acids recited in FIGS. 2A-2C. In certain embodiments, the antibody binds to a peptide comprising at least 3, 6, 9, 12, 10, 15, 20, 25, 30, 35, 40, 45, 50, 55, 60, 70, 80, 90, 100 or more contiguous amino acids recited in FIGS. 2A-2C. In one embodiment, the antibody is a monoclonal antibody. In another embodiment, the antibody is a humanized monoclonal antibody.

In another aspect, the invention provides an antigen that binds to an isolated peptide comprising at least 3 contiguous amino acids recited in FIGS. 2A-2C. In certain embodiments, the antigen binds to a peptide comprising at least 5, 10, 15, 20, 25, 30, 35, 40, 45, 50, 55, 60, 70, 80, 90, 100 or more contiguous amino acids recited in FIGS. 2A-2C.

In another aspect, the invention provides an isolated polypeptide complex comprising a puf-A polypeptide comprising at least three contiguous amino acids recited in FIGS. 2A-2C and a second polypeptide selected from the group consisting of caspase3, zgc:193933, prdm1a, spata2, tex10, rbb4, ddx3, zp2.2, HtrA2 and Blimp-1. In one embodiment, the second polypeptide is Blimp-1.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

FIG. 1 shows the cDNA nucleotide (SEQ ID NO:3) and amino acid (SEQ ID NO:4) sequence of the zebra fish puf-A gene.

FIGS. 2A-2C shows the human Puf-A nucleotide (SEQ ID NO:1) and amino acid (SEQ ID NO:2) sequences. The Puf domain comprising Leu165-Glu460 is highlighted in the boxed sequence.

DETAILED DESCRIPTION OF THE INVENTION

Figure 3:
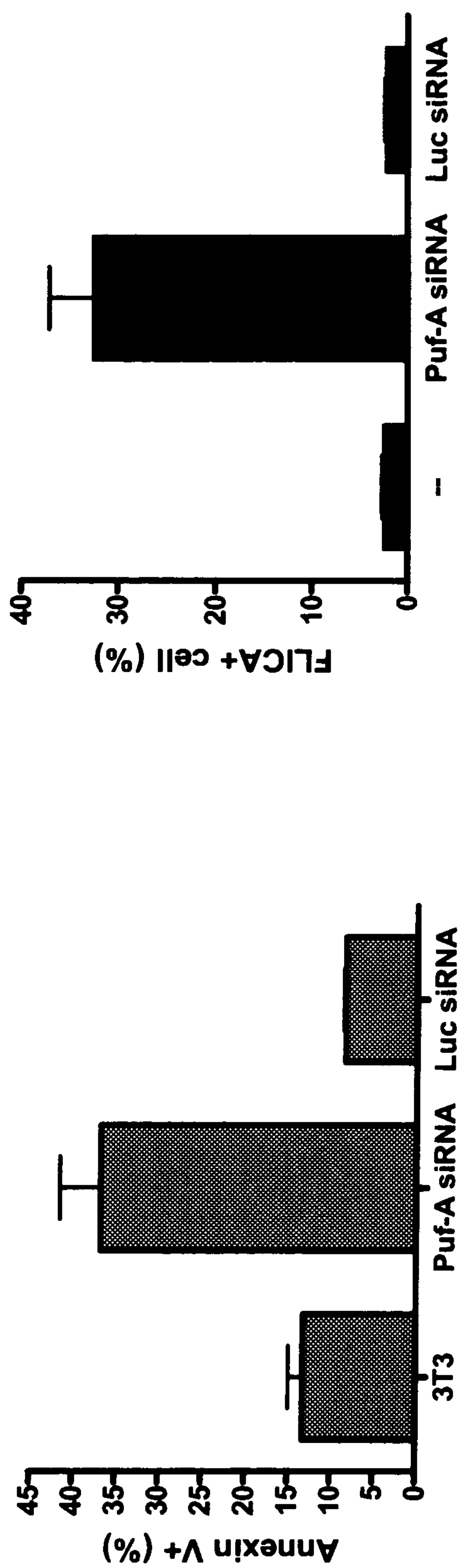
FIG. 3 shows the effect of Puf-A siRNA on induced cell apoptosis and caspase activation in mouse 3T3.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Because the newly found human gene, Puf-A, is expressed in retinal ganglion and pigmented cells of eye tissues and displays a unique anti-apoptotic activity, Puf-A genes and related derivatives serve as the targets for developing new therapeutic products for age-related and sight-threatening eye diseases. Regardless of the nature of the age-related retinopathies which patients are developing, by targeting and preventing the ultimate death of the cells in retina, one will be able to retain function in the photoreceptors and diminish the possibility of vision loss.

Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The practice of the present invention will employ, unless otherwise indicated, conventional techniques of molecular biology, microbiology, recombinant DNA, and immunology, which are within the skill of the art. Such techniques are explained fully in the literature. See, for example, Molecular Cloning A Laboratory Manual, 2nd Ed., ed. by Sambrook, Fritsch and Maniatis (Cold Spring Harbor Laboratory Press: 1989); DNA Cloning, Volumes I and II (D. N. Glover ed., 1985); Oligonucleotide Synthesis (M. J. Gait ed., 1984); Mullis et al. U.S. Pat. No. 4,683,195; Nucleic Acid Hybridization (B. D. Hames & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the treatise, Methods In Enzymology (Academic Press, Inc., N.Y.); Gene Transfer Vectors For Mammalian Cells (J. H. Miller and M. P. Calos eds., 1987, Cold Spring Harbor Laboratory); Methods In Enzymology, Vols. 154 and 155 (Wu et al. eds.), Immunochemical Methods In Cell And Molecular Biology (Mayer and Walker, eds., Academic Press, London, 1987); and Handbook Of Experimental Immunology, Volumes I-IV (D. M. Weir and C. C. Blackwell, eds., 1986).

As used herein, the term "polypeptide" refers to any multimer or polymer of amino acid residues. A polypeptide may be composed of two or more polypeptide chains. A polypeptide includes a protein, a peptide, and an oligopeptide. A polypeptide can be linear or branched. A polypeptide can comprise modified amino acid residues, amino acid analogs or non-naturally occurring amino acid residues and can be interrupted by non-amino acid residues. Included within the definition are amino acid polymers that have been modified, whether naturally or by intervention, e.g., formation of a disulfide bond, glycosylation, lipidation, methylation, acetylation, phosphorylation, or by manipulation, such as conjugation with a labeling component.

As used herein, the term "polynucleotide" refers to a single nucleotide or a polymer of nucleic acid residues of any length. The polynucleotide may contain deoxyribonucleotides, ribonucleotides, and/or their analogs and may be double-stranded or single stranded. A polynucleotide can comprise modified nucleic acids (e.g., methylated), nucleic acid analogs or non-naturally occurring nucleic acids and can be interrupted by non-nucleic acid residues. For example a polynucleotide includes a gene, a gene fragment, cDNA, isolated DNA, mRNA, tRNA, rRNA, isolated RNA of any sequence, recombinant polynucleotides, primers, probes, plasmids, and vectors. Included within the definition are nucleic acid polymers that have been modified, whether naturally or by intervention.

As used herein, the term "specifically binding," refers to the interaction between binding pairs (e.g., an antibody and an antigen). In various instances, specifically binding can be embodied by an affinity constant of about 10-6 moles/liter, about 10-7 moles/liter, or about 10-8 moles/liter, or less.

As used herein, the terms "RNAi," "siRNA," and "shRNA," refer to a RNA polynucleotides, small interfering RNA or short hairpin RNA, respectively. RNAi, siRNA and shRNA are used in various methods of RNA interference for gene silencing, as described in more detail below.

Puf A-Related Sequences

Zebrafish Puf-A nucleic acid and protein sequences are shown in FIG. 1. The full-length sequence of zebrafish puf-A DNA was identified using 5'- and 3'RACE. The 5'-untranslated region (UTR) and 3'-UTR are shown in lowercase letters and the coding region (nucleotides 45-1924) in uppercase letters. The stop codon is marked with an asterisk (*). The deduced amino acid sequence (629 amino acids) is shown below the nucleotide sequence. At residues 558-562, the sequence "Glu-Arg-Phe-Ser-Arg" is shown in bold letters.

A search for Puf-A-related sequence fragments in the databases suggested that the Puf-A in zebrafish is a member of the Puf family. 14 Puf-related proteins of zebrafish, mouse, and human were identified using the SMART server (Table 1). Sequence similarities among these Puf proteins in each cluster were analyzed and categorized (Kuo et al. (2009)). In this study, the human and mouse Puf-A homologs, i.e., KIAA0020 and D19Bwg1357e in Table 1, are designated, respectively, as the human and murine Puf-A, respectively. BLASTP analysis revealed that human Puf-A shared 89% identity in the aligned 647 amino acid residues with murine Puf-A and 66% identity with zebrafish Puf-A in the aligned 621 residues.

TABLE 1

INFORMATION ON THE PUTATIVE PUF PROTEINS IN HUMANS, MICE, AND ZEBRAFISH.

| SPECIES | PUF PROTEINS | Gene ID[a] | Gene location[a] | Accession #s of protein sequences | Length (amino acids) | Number of Puf repeats[d] |
|---|---|---|---|---|---|---|
| Human | PUF-A (KIAA0020) | 9933 | 9p24.2 | Q15397[b] | 648 | 6 |
| | C14ORF21 | 161424 | 14q12 | Q86U38[b] | 636 | 7 |
| | PUMILIO (PUM1) | 9698 | 1p35.2 | Q14671[b] | 1,186 | 8 |
| | PUM2 | 23369 | 2p22-p21 | Q8TB72[b] | 1,066 | 8 |
| Mouse | PUF-A (D19BWG1357E) | 52874 | 19 | Q8BKS9[b] | 647 | 6 |
| | 2610027L16RIK | 67842 | 14 | Q8BMC4[b] | 636 | 5 |
| | PUMILIO (PUM1) | 80912 | 4 | Q80U78[b] | 1,189 | 8 |
| | PUM2 | 80913 | 12 | Q80U58[b] | 1,066 | 8 |
| Zebrafish | PUF-A[e] | 394185 | 10 | XP_695580.2[c] | 629 | 6 |
| | LOC564287 | 564287 | 3 | XP_692728.2[c] | 604 | 5 |
| | LOC568777 | 568777 | 16 | XP_697221.2[c] | 457 | 4 |
| | LOC567494 | 567494 | 13 | NP_001096040.1[c] | 1,106 | 6 |
| | LOC569578 | 569578 | 20 | XP_698067.2[c] | 164 | 3 |
| | LOC798171 | 798171 | 18 | XP_001338629.1[c] | 182 | 3 |

[a]annotations described in the entrez gene database at NCBI.
[b]accession number used in SWISS-PROT.
[c]accession number used in the ref seq database.
[d]the puf repeats were identified by the SMART server.
[e]according to the annotations in entrez gene database, the old gene symbol for puf-A is "zgc: 66377" and the name for protein is "hypothetical protein loc394185".

The computer model of human Puf-A predicted its structure to be composed of six Puf repeats, each of which constitutes a unique superhelix, half doughnut-shaped Puf domain. The six Puf repeats are distributed in two separate regions from Leu-165 to Glu-273, and from Ala-350 to Glu-460 (R1 to 3 and R4 to 6, respectively. Each repeat has three helices and the second helix, which is located at the inner, concave face of the model, and interacts with RNA exhibiting characteristic features of a conventional Puf repeat (Wang X, Zamore P D, Hall T M (2001) Crystal structure of a Pumilio homology domain. Mol Cell 7: 855-865.) On the other hand, the sequence from Glu-274 to Glu-349, which represents the middle region of this model contains no typical Puf repeats identifiable by the SMART server. Detailed analysis of this model showed that this middle region possesses a length of segment close to two tandem Puf repeats (76 residues) and each of these "repeat-like" structures exhibits features of three-helix similar to a typical Puf repeat. It is concluded that this middle region mimics two Puf repeats structurally. Thus, the overall structure of Puf-A features a six-Puf-repeat domain with an intermediate region of two repeatlike segments so that it displays a topology similar to the conventional eight-repeat Pumilio homolog domain (Id.). Furthermore, this computer model of human Puf-A predicts that it is a new RNA-binding protein, distinctly different from the Pumilio domain. The Puf domain comprising Leu165-Glu460 is highlighted in the boxed sequence in FIGS. 2A-2C.

In addition, the values of electrostatic potentials on the molecular surface of human Puf-A were calculated. An asymmetric distribution of electrostatic potentials was noted for the Puf domain of Puf-A: its concave surface has predominately positive basic electrostatic potentials, presumably for RNA binding.

Puf A Molecules of the Present Invention

The agents of the present invention (collectively referred to as "Puf-A molecules") are capable of reducing or inhibiting or suppressing apoptosis in cells. As such, they may be used for a wide range of therapies and applications.

The Puf-A molecules of the present invention include Puf-A nucleic acid molecules (e.g., Puf-A encoding nucleic acid molecules, Puf-A fragment encoding molecules, Puf-A fusion encoding molecules, Puf-A antisense molecules, Puf-A triplex repressor molecules, etc.), Puf-A protein molecules (i.e. Puf-A and its fusions and fragments, antibodies to such molecules, and protein analogs and peptidomimetics of such molecules), and non-protein mimetics and analogs of such molecules.

The human Puf-A sequence is shown in FIGS. 2A-2C. The sequence is available in standard databases as Entrez ID (mRNA): NM_014878.4 and Swiss prot (protein): Q15397. The Puf domain comprising Leu165-Glu460 is highlighted in the boxed sequence.

Such molecules may either naturally occurring or non-naturally occurring. A naturally occurring Puf-A-1 molecule may be purified, such that one or more molecules that is or may be present in a naturally occurring preparation containing the molecule has been removed or is present at a lower concentration than that at which it would normally be found.

The molecules of the present invention may be nucleic acids, proteins, or organic molecules that have a tertiary structure which resembles or mimics the structure of a Puf-A protein molecule. The present invention further concerns the use of biologically active fragments of molecules, such as Puf-A nucleic acid molecules, Puf-A protein molecules, etc. in lieu of or in addition to any naturally occurring Puf-A molecule. As used herein, a molecule is said to be "biologically active" with respect to cellular proliferation if it is capable of mediating an effect on the apoptotic activity in a recipient cell. Such biological activity may be a structural attribute, such as the capacity to mediate antisense repression, or the ability to bind at a particular nucleic acid site, or with a particular active site of a protein, receptor, etc. (or to compete with another molecule for such binding) Alternatively, such an attribute may be catalytic, and involve the capacity of the biologically active molecule to mediate a chemical reaction or response in a recipient cell.

The present invention permits the isolation of all such Puf-A molecules in a "purified" form. As used herein, a Puf-A molecule is said to be "purified" if it is present in a preparation that lacks a molecule that is normally associated with the Puf-A molecule in its natural state. Proteins, lipids, nucleic acid sequences that do not encode Puf-A molecules are examples of molecules that are naturally associated with Puf-A molecules.

A preferred class of Puf-A nucleic acid molecules includes biologically active fragments thereof. To identify such fragments, the Puf-A nucleic acid molecules can be cleaved, as by mechanical methods or more preferably restriction endonuclease cleavage to thereby generate candidate fragments. Such fragments can then be provided to cells, and monitored for their capacity to inhibit DNA synthesis. In one embodiment, gene sequences that encode fragments of protein Puf-A molecules can be administered to a recipient cell.

By administering fragments of nucleic acid Puf-A molecules (with or without linked sequences) it is possible to assess whether a particular fragment of a Puf-A nucleic acid molecule has biological activity due to its structure.

Through the use of such methods, nucleic acid molecules that encode the amino terminal half of Puf-A-1 have been found to exhibit the capacity to convert immortalized cells or tumor cells to a quiescent state. More specifically, nucleic acid molecules that encode Puf-A amino acid residues 1-629 have been found to be capable of inhibiting cellular apoptosis. Preferred candidate oligonucleotide fragments include nucleic acid molecules that encode any contiguous 5, 10, 15, 20, 25, 30, 35, 40, 45, 50, 60, 70, 80, 90, 100 or more contiguous Puf-A amino acid residues.

One aspect of the present invention concerns methods for determining the level of Puf-A mRNA. Nucleic acid molecules that are capable of hybridizing to a Puf-A nucleic acid molecules can be used for such diagnostic purposes. As used herein, two nucleic acid molecules are said to be capable of hybridizing to one another if the two molecules are capable of forming an anti-parallel, double-stranded nucleic acid structure. The molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. As will be appreciated, complementary molecules need not exhibit "complete complementarity" (i.e. wherein every nucleotide of one of the molecules is complementary to a nucleotide of the other), but need only be sufficiently complementary in sequence to be able to form a stable double-stranded structure under defined solvent and salt concentrations. A nucleic acid molecule is said to be the "complement" of another nucleic acid molecule if they exhibit complete complementarity. Conventional stringency conditions are described by Sambrook, J., et al., (In: Molecular Cloning, a Laboratory Manual, 2nd Edition, Cold Spring Harbor Press, Cold Spring Harbor, N.Y. (1989)), and by Haymes, B. D., et al. (In: Nucleic Acid Hybridization, A Practical Approach, IRL Press, Washington, D.C. (1985)), both herein incorporated by reference). The nucleic acid molecules that can be used to hybridize to an Puf-A nucleic acid molecule will preferably be shorter than such Puf-A molecule. Preferred molecules will be completely complementary to an Puf-A nucleic acid molecule, and will have a length of between about 15 to about 250 nucleotides, and most preferably about 15 to about 30 nucleotides. Such nucleic acid molecules may be obtained using solid phase oligonucleotide synthetic methods, however such molecules can be obtained via the polymerase-mediated, template-dependent extension of a primer molecule that is complementary to a fragment of an Puf-A nucleic acid molecule.

The present invention further includes the proteins and polypeptides encoded by the Puf-A nucleic acid molecules or their oligonucleotide fragments. The sequences of Puf-A nucleic acid molecules permits one to ascribe and identify encoded protein and polypeptide molecules that can be used either to suppress apoptosis or to induce such states in cells. The amino acid sequence of such molecules can be readily derived from the known relationship between the nucleotide sequence of a nucleic acid molecule, and the amino acid sequence of the protein it encodes. Therapeutically active proteins and polypeptides can be identified using a method that is analogous to the above-described method for identifying therapeutically active Puf-A nucleic acid fragments. By mutating such proteins, it is possible to identify molecules that have lost the capacity to inhibit apoptosis. Among such mutated molecules will be proteins that are capable of exerting a dominant effect sufficient to mimic the effect of Puf-A-encoded proteins and polypeptides.

Typically, the Puf-A proteins and protein fragments will be produced free of any additional amino acid residues. Alternatively, the Puf-A proteins and protein fragments may be produced fused to an amino acid or to a polypeptide. Such synthesis may be accomplished using conventional peptide synthetic means, or, more preferably, using recombinant methods. Where fusion molecules are desired, such molecules may contain selectable cleavage sites such that the Puf-A portion of the fusion molecule may be cleaved from the remaining portion(s) of the fusion protein.

The present invention also pertains to "functional analogs" of the Puf-A molecules. Such analogs include both "classical analogs" and "mimetic analogs." A classical analog of an Puf-A molecule is one that has a similar biological activity, and is chemically related to the Puf-A molecule. By way of illustration, a non-naturally occurring mutant protein having Puf-A activity would comprise a classical analog of a protein Puf-A molecule. Similarly, a mutated Puf-A nucleic acid molecule would comprise an example of a classical analog of an Puf-A gene sequence. Likewise, an Puf-A molecule isolated from a non-human mammalian species (such as a mouse, monkey, etc.) would comprise an example of a classical analog of an Puf-A gene sequence. In contrast, a "mimetic analog" of an Puf-A molecule retains the biological activity of the molecule, but will typically be unrelated chemically. An organic molecule whose structure mimics the active site of an Puf-A protein would comprise a "mimetic analog" of that protein. Similarly, non-nucleic acid molecules capable of binding to a nucleic acid binding site of Puf-A, or recognized by Puf-A would be a mimetic analog of that molecule.

Thus, functional analogs may be either an oligonucleotide or polynucleotide, a proteinaceous compound (including both glycosylated and non-glycosylated proteins), or a non-proteinaceous compound (such as a steroid, a glycolipid, etc.) provided that the agent mimics the function of either an entire Puf-A nucleic acid molecule, or an oligonucleotide or polynucleotide fragment thereof, or a protein or polypeptide encoded by such a molecule or fragment. Preferred classical analogs include polypeptides (including circular as well as linear peptides) whose sequences comprise the active catalytic or binding sites of an Puf-A protein, or oligonucleotide fragments of nucleic acid Puf-A molecules that are capable of either repressing or inducing Puf-A activity. Preferred peptidomimetic analogs include polypeptides that are not fragments of an Puf-A protein, or mutants thereof, but nevertheless exhibit a capacity to inhibit apoptosis in an Puf-A-like manner, or to induce cellular proliferation in the manner of an Puf-A target protein antagonist.

Classical analogs can be identified either rationally, as described below, or via established methods of mutagenesis (see, for example, Watson, J. D. et al., Molecular Biology of the Gene, Fourth Edition, Benjamin/Cummings, Menlo Park, Calif. (1987). Significantly, a random mutagenesis approach requires no a priori information about the gene sequence that is to be mutated. This approach has the advantage that it assesses the desirability of a particular mutant on the basis of its function, and thus does not require an understanding of how or why the resultant mutant protein has adopted a particular conformation. Indeed, the random mutation of target gene sequences has been one approach used to obtain mutant proteins having desired characteristics (Leatherbarrow, R. J. Prot. Eng. 1:7-16 (1986); Knowles, J. R., Science 236:1252-1258 (1987); Shaw, W. V., Biochem. J. 246:1-17 (1987); Gerit, J. A. Chem. Rev. 87:1079-1105 (1987)). Alternatively, where a particular sequence alteration is desired, methods of site-directed mutagenesis can be employed. Thus, such methods may be used to selectively alter only those amino acids of the protein that are believed to be important (Craik, C. S., Science 228:291-297 (11385); Cronin, C. S. et al., Biochem. 27:4572-4579 (1988); Wilks, H. M. et al., Science 242:1541-1544 (1988)).

The present invention thus also pertains to antagonists of the targets of pufA molecules. Such antagonists may comprise Puf-A target analogs that compete with, or that inhibit Puf-A target function. Alternatively, such antagonists may comprise analogs of molecules such as Puf-A. Any of a variety of methods can be used to identify polypeptides or non-proteinaceous molecules that inhibit or repress Puf-A target function.

The present invention thus also pertains to protagonists of the Puf-A molecules. As used herein, a "protagonist" of a Puf-A molecule is a molecule that enhances or increases the biological activity of an Puf-A molecule.

One aspect of the present invention concerns antibodies to Puf-A target proteins and protein fragments and the diagnostic and therapeutic uses of such antibodies. Where the antibodies or their fragments are intended for therapeutic purposes, it may desirable to "humanize" them in order to attenuate any immune reaction. Humanized antibodies may be produced, for example by replacing an immunogenic portion of an antibody with a corresponding, but non-immunogenic portion (i.e. chimeric antibodies) (Robinson, R. R. et al., PCT Patent Publication PCT/US86/02269; Akira, K. et al., European Patent Application 184,187; Taniguchi, M., European Patent Application 171,496; Morrison, S. L. et al., European Patent Application 173,494; Neuberger, M. S. et al., PCT Application WO 86/01533; Cabilly, S. et al., European Patent Application 125,023; Better, M. et al., Science 240:1041-1043 (1988); Liu, A. Y. et al., Proc. Natl. Acad. Sci. USA 84:3439-3443 (1987); Liu, A. Y. et al., J. Immunol. 139:3521-3526 (1987); Sun, L. K. et al., Proc. Natl. Acad. Sci. USA 84:214-218 (1987); Nishimura, Y. et al., Canc. Res. 47:999-1005 (1987); Wood, C. R. et al., Nature 314:446-449 (1985)); Shaw et al., J. Natl. Cancer Inst. 80:1553-1559 (1988); all of which references are incorporated herein by reference). General reviews of "humanized" chimeric antibodies are provided by Morrison, S. L. (Science, 229:1202-1207 (1985)) and by Oi, V. T. et al., BioTechniques 4:214 (1986); which references are incorporated herein by reference).

In one therapeutic embodiment, chimeric bivalent antibodies are employed which contain two different Fab regions, such that the antibody is capable of binding to a Puf-A target epitope (via the first such Fab region) and to a "non-Puf-A target epitope" (i.e. an epitope of a protein other than a Puf-A target protein) (via the second such Fab region). In one embodiment, such "non-Puf-A target epitopes" are selected such that the chimeric molecule can bind to cellular receptors, such as hormone receptors, immune response receptors, etc. Particularly preferred non-Puf-A target receptors include cellular antigens that are indicative of apoptosis. The above-described Puf-A target proteins and protein fragments may be used to elicit the production of antibodies, single-chain antigen binding molecules, or other proteins capable of binding an SDI epitope. Such antibodies may be polyclonal or monoclonal, and may comprise intact immunoglobulins, of antigen binding portions of immunoglobulins (such as (F(ab'), F(ab') 2) fragments, or single-chain immunoglobulins producible, for example, via recombinant means.

RNA interference is now established as an important biological strategy for gene silencing, but its application to mammalian cells has been limited by nonspecific inhibitory effects of long double-stranded RNA on translation. Moreover, delivery of interfering RNA has largely been limited to administration of RNA molecules. Hence, such administration must be performed repeatedly to have any sustained effect.

RNA interference (hereinafter "RNAi") is a method of post-transcriptional gene regulation that is conserved throughout many eukaryotic organisms. RNAi is induced by short (i.e., <30 nucleotide) double stranded RNA ("dsRNA") molecules which are present in the cell (Fire A et al. (1998), Nature 391: 806-811). These short dsRNA molecules, called "short interfering RNA" or "siRNA," cause the destruction of messenger RNAs ("mRNAs") which share sequence homology with the siRNA to within one nucleotide resolution (Elbashir S M et al. (2001), Genes Dev, 15: 188-200). It is believed that the siRNA and the targeted mRNA bind to an "RNA-induced silencing complex" or "RISC", which cleaves the targeted mRNA. The siRNA is apparently recycled much like a multiple-turnover enzyme, with one siRNA molecule capable of inducing cleavage of approximately 1000 mRNA molecules. siRNA-mediated RNAi degradation of an mRNA is therefore more effective than currently available technologies for inhibiting expression of a target gene.

Elbashir S M et al. (2001), supra, have shown that synthetic siRNA of 21 and 22 nucleotides in length, and which have short 3' overhangs, are able to induce RNAi of target mRNA in a *Drosophila* cell lysate. Cultured mammalian cells also exhibit RNAi degradation with synthetic siRNA (Elbashir S M et al. (2001) Nature, 411: 494-498), and RNAi degradation induced by synthetic siRNA has recently been shown in living mice (McCaffrey A P et al. (2002), Nature, 418: 38-39; Xia H et al. (2002), Nat. Biotech. 20: 1006-1010). The therapeutic potential of siRNA-induced RNAi degradation has been demonstrated in several recent in vitro studies, including the siRNA-directed inhibition of HIV-1 infection (Novina C D et al. (2002), Nat. Med. 8: 681-686) and reduction of neurotoxic polyglutamine disease protein expression (Xia H et al. (2002), supra).

Disclosed herein is a strategy that results in substantial silencing of targeted alleles via siRNA. Use of this strategy results in markedly diminished in vitro and in vivo expression of targeted alleles. This strategy is useful in reducing expression of targeted alleles in order to model biological processes or to provide therapy for human diseases. As used herein the term "substantial silencing" means that the mRNA of the targeted allele is inhibited and/or degraded by the presence of the introduced siRNA, such that expression of the targeted allele is reduced by about 10% to 100% as compared to the level of expression seen when the siRNA is not present. Generally, when an allele is substantially silenced, it will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, 98%, 99% or even 100% reduction expression as compared to when the siRNA is not present. As used herein the term "substantially normal activity" means the level of expression of an allele when an siRNA has not been introduced to a cell.

One of skill in the art can select target sites for generating siRNA specific for other alleles beyond those specifically described in the experimental examples. Such allele-specific siRNAs made be designed using the guidelines provided by Ambion (Austin, Tex.). Briefly, the target cDNA sequence is scanned for target sequences that had AA di-nucleotides. Sense and anti-sense oligonucleotides are generated to these targets (AA+3' adjacent 19 nucleotides) that contained a G/C content of 35 to 55%. These sequences are then compared to others in the human genome database to minimize homology to other known coding sequences (BLAST search).

To accomplish intracellular expression of the therapeutic siRNA, an RNA molecule is constructed containing two complementary strands or a hairpin sequence (such as a 21-bp hairpin) representing sequences directed against the gene of interest. The siRNA, or a nucleic acid encoding the siRNA, is introduced to the target cell, such as a diseased brain cell. The siRNA reduces target mRNA and protein expression.

The construct encoding the therapeutic siRNA is configured such that the one or more strands of the siRNA are encoded by a nucleic acid that is immediately contiguous to a promoter. In one example, the promoter is a pol II promoter. If a pol II promoter is used in a particular construct, it is selected from readily available pol II promoters known in the art, depending on whether regulatable, inducible, tissue or cell-specific expression of the siRNA is desired. The construct is introduced into the target cell, such as by injection, allowing for diminished target-gene expression in the cell.

Puf-A Protein Targets

The biotinylated puf-A was prepared by transcription/translation in vitro and then purified through immobilization on streptavidin magnetic beads. Afterwards, the purified biotinylated puf-A were mixed with 10 μg mRNA mixtures from embryos and ovaries. After fix and PBS wash, the residual RNA pulled down by biotinylated Puf-A was amplified, subcloned and sequenced. Using this pull-down assay, many potential RNA targets for puf-A bindings were found and listed in Table 2 with their gene IDs and symbols. We further showed that there was a reciprocal relationship for the expression of puf-A and one of its potential RNA targets, prdm1a. (Jui-Chin Chang and John Yu, unpublished observations). Therefore, these results and computer modeling predict that puf-A is a RNA binding protein.

TABLE 2

The potential target RNAs identified from pull down assay with biotinylated puf-A

| Gene IDs | Gene symbols | Names or descriptions | Locations (chromosome) |
|---|---|---|---|
| 792333 | zgc:193933 | ovary-expressed homeobox protein | 24 |
| 323473 | prdm1a | PR domain containing 1, with ZNF domain | 16 |
| 568830 | spata2 | spermatogenesis associated 2 | 23 |
| 327196 | tex10 | testis expressed 10 | 16 |
| 321726 | rbb4 | retinoblastoma binding protein 4 | 19 |
| 566947 | ddx3 | DEAD (Asp-Glu-Ala-Asp) box polypeptide 3 | 9 |
| 114438 | zp2.2 | zona pellucida glycoprotein 2.2 | 20 |

Puf-A Protein Target HtrA2

In one embodiment the invention relates to chemical compounds that either enhance the expression of Puf-A or affect its downstream targets (e.g. HtrA2), thereby preventing retinal apoptosis.

The serine protease HtrA2/Omi is released from the mitochondrial intermembrane space following apoptotic stimuli. Once in the cytosol, HtrA2/Omi has been implicated in promoting cell death by binding to inhibitor of apoptosis proteins (IAPs) via its amino-terminal Reaper-related motif, thus inducing caspase activity, and also in mediating caspase-independent death through its own protease activity. (Hegde, R., S. M. Srinivasula, Z. Zhang, R. Wassell, R. Mukattash, L. Cilenti, G. DuBois, Y. Lazebnik, A. S. Zervos, T. Fernandes-Alnemri, and E. S. Alnemri. 2002. Identification of Omi/HtrA2 as a mitochondrial apoptotic serine protease that disrupts inhibitor of apoptosis protein-caspase interaction. J. Biol. Chem. 277:432-438.)

Studies of the mechanism of Puf-A mediated anti-apoptosis, co-immunoprecipitation and gene expression microarray analysis showed that HtrA2 is the binding target of Puf-A, suggesting the feasibility of cell-based assay to screen for effective small molecules for manipulating anti-apoptotic process. Therefore, these two approaches hold tremendous promise for the treatment of human retinal diseases.

Therapeutic Uses of Puf-A

The terms “treatment,” “therapy,” and “medical use” may cover prophylaxis. “Treatment,” “therapy” and “medical use” may also cover inhibition of a disease or disorder, protection against a disease or disorder, and/or prevention (not absolute) of a disease or disorder, and/or prevention of the progression of a disease or disorder. “Treatment”, “therapy” and “medical use” may also include curative, ameliorative, and/or symptomatic treatment, therapy and medical use.

In humans, a number of diseases of the retina involve the progressive degeneration and eventual death of photoreceptors, leading inexorably to blindness. Degeneration of photoreceptors, such as by inherited retinal dystrophies (e.g., retinitis pigmentosa), age-related macular degeneration and other maculopathies, or retinal detachment, are all characterized by the progressive atrophy and loss of function of photoreceptor outer segments. In addition, death of photoreceptors or loss of photoreceptor function results in partial deafferentation of second order retinal neurons (rod bipolar cells and horizontal cells) in patients with retinal dystrophies, thereby decreasing the overall efficiency of the propagation of the electrical signal generated by photoreceptors. Factors that are capable of rescuing photoreceptors, bipolar cells, horizontal cells, amacrine cells or ganglion cells from cell death and/or restoring the function of dysfunctional (atrophic or dystrophic) photoreceptors, bipolar cells, horizontal cells, amacrine cells or ganglion cells may represent useful therapies for the treatment of such conditions.

The molecules of the present invention possess therapeutic utility. A use is said to be therapeutic if it alters a physiologic condition. Puf-A prevents apoptosis by blocking the action of caspases, which are enzymes involved in the cell death pathway. Puf-A nucleic acid molecules, their fragments, encoded proteins and polypeptides, and analogs have use in providing neuronal protection for retinal cells. Therefore, intraocular delivery of Puf-A gene and related truncated fragment sequences/chemical compounds can provide neuronal protection for retinal cells due to its specific anti-apoptotic activity.

A wide variety of other disease states are known by those of ordinary skill in the art, such as those described in Goodman & Gilman, THE PHARMACOLOGICAL BASIS OF THERAPEUTICS (McGraw Hill, 2001), and REMINGTON’S PHARMACEUTICAL SCIENCES (Lippincott Williams & Wilkins; 21st ed., 2005). Those to which the present invention may be applied may be determined by those with ordinary skill in the art without undue experimentation.

In one embodiment, such treatment is accomplished by providing Puf-A protein or protein fragments to ocular cells. Such protein may be provided directly, since Puf-A may be capable of directly entering such cells. Alternatively, Puf-A may be provided in liposomes, viral sheaths, or other vehicles. In a second embodiment, gene sequences that encode Puf-A or fragments of Puf-A may be provided as a gene therapy for age-related and sight-threatening eye diseases.

For such uses, it is desirable to employ Puf-A molecules that can be administered by intra-ocular means (such as by eye drops, or ointments). The ability of a drug to traverse the cornea is enhanced if the drug has both lipophilic and hydrophilic regions. Thus, for intra-ocular delivery, it is desirable to modify the Puf-A molecules of the invention such that they contain such regions. Suitable lipophilic and hydrophilic groups are known in the art (see, Remington: The Science and Practice of Pharmacy (21st Edition, 2005)), and comprise aliphatic groups, lipids, etc. (lipophilic groups) and organic acids, esters, ionic groups, etc. (hydrophilic groups). Such groups can be readily added to the Puf-A molecules of the present invention by, for example, derivatizing the side chain groups of appropriate amino acids.

Another approach to the intracellular delivery of biologically active molecules involves the use of cationic polymers. Rothbard et al., U.S. Patent Application Publication No. 20030022831, describes certain poly-lysine and poly-arginine compounds for intra-ocular delivery of drugs.

Cysteinyl residues may be reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues may be derivatized by reaction with diethylprocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino terminal residues may be reacted with succinic or other carboxylic acid anhydrides. Derivatization with these agents has the effect of reversing the charge of the lysinyl residues. Other suitable reagents for derivatizing a-amino-containing residues include imidoesters such as methyl picolinimidate; pyridoxal phosphate; pyridoxal; chloroborohydride; trinitrobenzenesulfonic acid; O-methylisurea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pK.sub.a of the guanidine functional group. Furthermore, these reagents may react with the groups of lysine as well as the arginine epsilon-amino group.

Carboxyl side groups (aspartyl or glutamyl) may be selectively modified by reaction with carbodiimides (R'—N—C—N—R') such as 1-cyclohexyl-3-(2-morpholinyl-(4-ethyl)carbodiimide or 1-ethyl-3 (4 azonia 4,4-dimethylpentyl) carbodiimide. Furthermore, aspartyl and glutamyl residues may be converted to asparaginyl and glutaminyl residues by reaction with ammonium ions.

A number of different animal models that attempt to replicate one or more features of macular degeneration, diabetic retinopathy, and/or choroidal neovascularization are known in the art. A compound of the invention can be administered in various doses to mice, rats, dogs, primates, etc. that have either spontaneous or macular degeneration and/or choroidal neovascularization or in which macular degeneration and/or choroidal neovascularization have been induced by a treatment. The ability of the compound to prevent or treat one or more indicia of macular degeneration (e.g. CNV, accumulation of lipofuscin in and/or drusen beneath the RPE, photoreceptor atrophy or hypertrophy, altered RPE pigmentation, photoreceptor loss, altered electroretinogram, etc.) is assessed. Visual examination, photography, histopathology, immunohistology, etc., can be used. Animal models for other ocular conditions are also known in the art.

Useful models include animals in which choroidal neovascularization is induced by laser treatment (Bora, P. S., et al., Proc. Natl. Acad. Sci. 100(5): 2679-2684, 2003; Zacks, D N, et al., Invest Opthalmol V is Sci. 243(7):2384-91, 2002). Other models include animals that have been treated with a variety of agents such as lipid hydroperoxide (Tamai, K., et al., Exp Eye Res. 74(2):301-8, 2002), pellets comprising growth factors, etc. Animals genetically engineered to overexpress or underexpress one or more genes are also useful. For example, transgenic mice (mcd/mcd mice) that express a mutated form of cathepsin D that is enzymatically inactive display features associated with geographic atrophy (Rakoczy, P E, et al, Am. J. Path., 161(4), 1515-1524, 2002). Adeno-associated virus (AAV) mediated expression of vascular endothelial growth factor induces choroidal neovascularization in rats (Wang, F., et al., Invest Opthalmol V is Sci. 44(2):781-90, 2003). A preferred model is a transgenic mouse deficient in either monocyte chemoattractant protein (Ccl-2) or its cognate chemokine receptor (Ccr-2) (Ambati, J., et al., Nat Med. 9(11):1390-7, 2003; U.S. Ser. No. 10/685,705—U.S. publication 20040177387). Aged mice with a defiency in either of these proteins exhibit a number of features of ARMD including accumulation of lipofuscin in and drusen beneath the RPE, photoreceptor atrophy, and CNV. Methods for testing the efficacy of a candidate agent using this mouse model are disclosed in U.S. publication no. 20040177387. In general, a candidate agent is administered to the mouse either before or after development of features of ARMD, and at least one eye is monitored for development or regression of drusen and/or lipofuscin accumulation therein, for affect of the candidate agent on Bruch's membrane, affect on retinal degeneration, and/or for affect on choroidal neovascularization. The candidate agent can be administered systemically or locally. The agent can be delivered orally, intravenously, intraperitoneally, intravitreously, transsclerally or topically. The agent can be delivered by intravitreal injection, by subretinal injection or instillation, transclerally, by sustained release implant, etc. The eye can be analyzed by opthalmoscopy, angiography, histopathology or a combination thereof. Any of these methods can be used to assess efficacy of a candidate agent in any animal model. Models also exist for diabetic retinopathy. These examples are but a few of the model systems in which efficacy of the compounds of the invention can be assessed.

Compounds that show promising results in animal studies are tested in humans, e.g., using standard protocols and endpoints for clinical trials for therapies for conditions such as ARMD or diabetic retinopathy.

Because puf-A is expressed in retinal ganglion and pigmented cells of eye tissues and displays a unique and specific anti-apoptotic activity, Puf-A genes, derivatives and related compounds serve as the targets for developing new therapeutic or preventive products for eye diseases and blindness.

The compositions of the invention can be administered to a subject to treat a macular degeneration related condition, diabetic retinopathy, retinopathy of prematurity, persistent hyperplastic vitreous syndrome, choroidal neovascularization, uveitis, etc. Ancillary therapies may also be used concurrently, prior to, or following treatment using the compositions and methods of the invention. Such therapies include, but are not limited to, administration of antioxidant vitamin and/or mineral therapy, photodynamic therapy (e.g., with verteporfin or other agents), administration of antiinflammatory agents, antiangiogenic therapy (e.g., angiogenesis inhibitors such as anecortave acetate or other angiostatic steroids; rhuRab V2 ranibizumab pegaptanib sodium anti-VEGF or anti-VEGFR siRNA, antisense RNA, or aptamer; or any other antiangiogenic agent including but not limited to a small molecule, siRNA, antisense RNA, or aptamer targeted to any proangiogenic gene), growth factor administration, implantation of cells (e.g., neural stem cells, RPE stems cells, RPE cells) into the eye, laser photocoagulation, radiation therapy, thermal therapy, and surgery (e.g., submacular surgery or macular translocation). In certain embodiments of the invention a growth factor for RPE cells is administered, e.g., REF-1/TFPI-2 (Tanaka, Y, et al., Invest Opthalmol V is Sci. 45(1):245-52, 2004).

Methods of Administration of Puf-A

The Puf-A molecules of the present invention can be formulated according to known methods to prepare pharmaceutically useful compositions, whereby these materials, or their functional derivatives, having the desired degree of purity are combined in admixture with a physiologically acceptable carrier, excipient, or stabilizer. Such materials are non-toxic to recipients at the dosages and concentrations employed. The "Puf-A molecule" of such compositions may be Puf-A protein, fusions (e.g., GST-fusions, etc.) or fragments of Puf-A protein or peptidomimetics or non-protein mimetics of such molecules. The Puf-A molecules may be sense, antisense or triplex oligonucleotides of the Puf-A cDNA or gene. A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

In some instances, the presence of an intervening sequence upstream of a protein-encoding nucleic acid sequence can enhance the transcription or expression of specified polynucleotides (Brinster, R. L. et al., Proc Natl. Acad. Sci. (U.S.A.) 85:836-840 (1988); Palmiter, R. D. et al., Proc. Natl. Acad. Sci. (U.S.A.) 88:478-482 (1991); Huang, M. T. F. et al., Nucl. Acids Res. 18:937-947 (1990); GRuss et al., Proc. Natl. Acad Sci. (U.S.A.) 76:4317 (1979); Hamer, D. et al., Cell 18:1299 (1979); Gasser, et al., Proc. Natl. Acad. Sci. (U.S.A.) 79:6522 (1982); Calles, et al., Genes & Devel. 1:1183 (1987)). Where the Puf-A molecules that are to be administered comprise nucleic acid molecules, such as Puf-A-encoding molecules or Puf-A antisense sequences, it is particularly preferred to employ nucleic acid molecule that include at least one non-translated intervening sequence within, or adjacent to the relevant Puf-A sequence. Since expression is obtained in the absence of such intervening sequences, the relative position or number of intervening sequences is not critical to the invention. The presence of such a non-translated intervening sequence can, however, increase the extent of transcription and/or expression of Puf-A nucleic acid molecules. A preferred construct contains the Puf-A sequences adjacent to, but not interrupted by, the intervening sequences.

Suitable vehicles and their formulation, inclusive of other human proteins, e.g., human serum albumin, are described, for example, in Remington: The Science and Practice of Pharmacy (Lippincott Williams & Wilkins; 21st Edition, 2005). In order to form a pharmaceutically acceptable composition suitable for storage or administration, such compositions will contain an effective amount of one or more "Puf-A molecule."

If the composition is to be water soluble, it may be formulated in a buffer such as phosphate or other organic acid salt preferably at a pH of about 7 to 8. If the composition is only partially soluble in water, it may be prepared as a microemulsion by formulating it with a nonionic surfactant such as Tween®, Pluronics®, or PEG, e.g., Tween® 80, in an amount of, for example, 0.04-0.05% (w/v), to increase its solubility. The term "water soluble" as applied to the polysaccharides and polyethylene glycols is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

Optionally other ingredients may be added such as antioxidants, e.g., ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; and sugar alcohols such as mannitol or sorbitol.

Additional pharmaceutical methods may be employed to control the duration of action. Controlled or sustained release preparations may be achieved through the use of polymers to complex or absorb the Puf-A molecule(s) of the composition. The controlled delivery may be exercised by selecting appropriate macromolecules (for example polyesters, polyamino acids, polyvinyl pyrrolidone, ethylenevinylacetate, methylcellulose, carboxymethylcellulose, or protamine, sulfate) and the concentration of macromolecules as well as the methods of incorporation in order to control release.

Sustained release formulations may also be prepared, and include the formation of microcapsular particles and implantable articles. For preparing sustained-release compositions, the Puf-A molecule(s) of the composition is preferably incorporated into a biodegradable matrix or microcapsule. A suitable material for this purpose is a polylactide, although other polymers of poly-(α-hydroxycarboxylic acids), such as poly-D-(+3-hydroxybutyric acid (EP 133,988A), can be used. Other biodegradable polymers include poly(lactones), poly (orthoesters), polyamino acids, hydro-gels, or poly(orthocarbonates) poly(acetals). The polymeric material may also comprise polyesters, poly(lactic acid) or ethylene vinylacetate copolymers. For examples of sustained release compositions, see U.S. Pat. No. 3,773,919, EP 58,481A, U.S. Pat. No. 3,887,699, EP 158,277A, Canadian Pat. No. 1176565, U. Sidman et al., "Biopolymers" 22:547 [1983], and R. Langer et al, "Chem. Tech." 12:98 [1982].

Sustained release formulations including various ocular implants and other ocular drug delivery systems that are of use in various embodiments of the invention are described, for example, in U.S. Pat. Nos. 6,692,759; 6,331,313; 5,869,079; 5,824,072; and U.S. Ser. No. 10/918,597 (Pub. No. 20050048099); Ser. No. 10/837,357 (Pub. No. 20050244469); Ser. No. 11/092,122 (Pub. No. 20050244472) and Ser. No. 11/116,698 (Pub. No. 20050281861) as well as a number of other patents and publications referenced in the foregoing, all of which are incorporated herein by reference.

A method of making a sustained release formulation involves combining or mixing the therapeutic agent with a polymeric component to form a mixture. The mixture may then be extruded, compressed, molded, etc., to form a single composition. Optionally, heat and/or pressure can be used. The single composition may then be processed to form individual implants or particles suitable for placement in an eye of a patient. Additional methods for incorporating therapeutically active agents into polymeric matrices are known in the art. The polymeric matrix can be formed into various shapes such as rods, disks, wafers, etc., which may have a range of different dimensions (e.g., length, width, etc.) and volumes. Exemplary shapes include spherical, cylindrical, helical, coil-shaped or helical, screw-shaped, cubical, conical, ellipsoidical, biconvex, hemispherical or near-hemispherical etc.

Alternatively, instead of incorporating the Puf-A molecule(s) of the composition into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington: The Science and Practice of Pharmacy (21st Edition, 2005).

Liposomes are a particularly preferred means for accomplishing the delivery of Puf-A (protein or nucleic acid or other) molecules. Such a delivery means is particularly preferred when administering Puf-A molecules to skin as by topical administration. Although a wide variety of liposome compositions can be employed, a preferred liposome composition is composed of a mixture of positively charged and neutral lipids, such as those disclosed by Eppstein, D. A. et al. (U.S. Pat. No. 4,897,355), herein incorporated by reference. An alternative preferred liposome composition is described by Yarosh, D. B. (U.S. Pat. No. 5,190,762, herein incorporated by reference), and in particular the pH-sensitive liposomes discussed therein. Such sensitivity causes the liposomes to destabilize at a pH of less 4.5 Such sensitivity is produced by using phospholipids (such as phosphatidylethanolamine) which form lipid bilayers when charged, but fail to stack in an ordered fashion when neutralized. The net charge of such phospholipids can be maintained at a pH which would otherwise neutralize the phospholipid's head groups by including charged molecules in the lipid bilayer which themselves can become neutralized. Examples of suitable charged molecules include oleic acid and cholesteryl hemisuccinate (CHEMS) (U.S. Pat. No. 5,190,762).

Liposomes are artificial membrane vesicles which are useful as delivery vehicles in vitro and in vivo. In order for a liposome to be an efficient gene transfer vehicle, the following characteristics should be present: (1) encapsulation of the genetic material at high efficiency while not compromising the biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al. (1988) Biotechniques, 6:682). Examples of suitable lipid liposome production include phosphatidyl compounds, such as phosphatidylglycerol, phosphatidylcholine, phosphatidylserine, phosphatidylethanolamine, sphingolipids, cerebrosides, and gangliosides. Additional examples of lipids include, but are not limited to, polylysine, protamine, sulfate and 3b-[N—(N', N' dimethylaminoethane) carbamoyl] cholesterol.

A particularly preferred liposome having such a composition is Lipofectamine™ Reagent (Life Technologies, Inc., Gaithersburg, Md.). The positively charged and neutral lipids form liposomes that can complex with either acidic protein or nucleic acids (see, Lin, M. F. et al., Biochem. Biophys. Res. Commun. 192:413-419 (1993); Wizel, B. et al., Eur. J. Immunol. 24:1487-1495 (1994)). The capacity of such liposomes to deliver a basic protein such as Puf-A (predicted pI=8.4) is quite unexpected.

"Transferosomes" are also preferred liposomes for the purposes of the present invention. Methods for producing and using transferosomes are provided by Planas, M. E. et al. (Anesth. Analg. 75:615-621 (1992)), Cevc, G. et al. (Biochim Biophys. Acta 1104:226-232 (1992)), Blume, et al. (Biochim Biophys. Acta 1146:157-168 (1993)), Blume, et al. (Biochim Biophys. Acta 1149:180-184 (1993)), all herein incorporated by reference.

Additional liposome formulations are disclosed by Handjani, R. M. et al. (U.S. Pat. No. 4,830,857), Hope, M. J. et al. (U.S. Pat. No. 5,204,112; U.S. Pat. No. 5,252,263), and by Vanlerberghe, G., et al. (U.S. Pat. No. 5,164,488; U.S. Pat. No. 4,827,003; U.S. Pat. No. 5,008,406; U.S. Pat. No. 4,247,411), all herein incorporated by reference.

In one embodiment, particularly performed using the above-described preferred liposome compositions, preformed liposomes are incubated with Puf-A protein molecules. Without limitation to the invention, the protein is believed to unexpectedly adsorb to (or dissolve into) the external surface of the liposome, and to thus become arrayed on or in the liposome surface. The protein may traverse the surface of the liposome.

The liposome formulations can be administered to cells in culture (so as to achieve immortalization, or to induce the cessation of proliferation), or, therapeutically, to treat disease or hypo-proliferative conditions.

In one embodiment, such formulations will contain a Puf-A molecule (e.g., a GST-Puf-A fusion, etc.) that can mediate its own intracellular uptake. Suitable methods are known in the art, see, for example, by Biessen, E. A. L. et al. (PCT Application WO94/04545), Feigner, P. L. (PCT Patent Application WO91/17424), Akiyama, K. et al. (PCT Application WO93/20801), Blum, A. et al. (PCT Application WO93/04672), Abai, A. M. et al. (PCT Application WO93/03709), Hosokawa, S. et al. (U.S. Pat. No. 5,264,221), Cullis, P. R. et al. (U.S. Pat. No. 5,204,112; U.S. Pat. No. 5,252,263), Japanese Pat. No. 4,082,893, Phillips, W. T. et al. (U.S. Pat. No. 5,158,760), Weiner, N. D. (PCT Application WO91/01719), Hostetler, K. Y. et al. (U.S. Pat. No. 5,223,263), Kobayashi, Y. et al. (European Pat. No. 335597); Weiner, A. L. et al. (PCT Application WO89/05151); Hope, M. J. et al. (PCT Application WO87/07530), all herein incorporated by reference.

In a second embodiment, liposome formulations and methods that permit intracellular uptake of the Puf-A molecule will be employed. Suitable methods are known in the art, see, for example, Chicz, R. M. et al., (PCT Application WO 94/04557), Jaysena; S. D. et al. (PCT Application WO93/12234), Yarosh, D. B. (U.S. Pat. No. 5,190,762), Callahan, M. V. et al. (U.S. Pat. No. 5,270,052) and Gonzalezro, R. J. (PCT Application 91/05771), all herein incorporated by reference.

Puf-A also may be introduced in nucleic acid form. The invention also contemplates nucleic acid molecules that regulate the expression of puf-A or any gene that is a specific target of the Puf-A molecule. Nucleic acids can be introduced by incorporation into vectors for delivery into the target cells, preferably for intraocular delivery, including into the intravitreal space.

Some embodiments of the present invention utilize vectors that can be delivered to the ocular cells by using viral vectors or by using non-viral vectors. Preferred embodiments of the invention use adeno-associated viral (AAV) vectors comprising a nucleotide sequence encoding a chimeric receptor for gene delivery. Adeno-associated virus (AAV) has been used with success to deliver genes for gene therapy and clinical trials in humans have demonstrated great promise (see, e.g., Kay et al., Nat. Genet. (2000) 24:257-261). As the only viral vector system based on a nonpathogenic and replication-defective virus, recombinant AAV virions have been successfully used to establish efficient and sustained gene transfer of both proliferating and terminally differentiated cells in a variety of tissues without detectable immune responses or toxicity (Bueler, H., Biol. Chem. (1999) 380:613-622).

The AAV genome is a linear, single-stranded DNA molecule containing about 4681 nucleotides. The AAV genome generally comprises an internal nonrepeating genome flanked on each end by inverted terminal repeats (ITRs). The ITRs are approximately 145 base pairs (bp) in length. The ITRs have multiple functions, including as origins of DNA replication, and as packaging signals for the viral genome. The internal nonrepeated portion of the genome includes two large open reading frames, known as the AAV replication (rep) and capsid (cap) genes. The rep and cap genes code for viral proteins that allow the virus to replicate and package into a virion. In particular, a family of at least four viral proteins are expressed from the AAV rep region, Rep 78, Rep 68, Rep 52, and Rep 40, named according to their apparent molecular weight. The AAV cap region encodes at least three proteins, VP1, VP2, and VP3. AAV has been engineered to deliver genes of interest by deleting the internal nonrepeating portion of the AAV genome (i.e., the rep and cap genes) and inserting a heterologous gene between the ITRs.

The nucleotide sequences of AAV ITR regions are known. The ITR sequences for AAV-2 are described, for example by Kotin et al. (1994) Human Gene Therapy 5:793-801; Berns "Parvoviridae and their Replication" in Fundamental Virology, 2nd Edition, Raven Press, N.Y., 1990. The skilled artisan will appreciate that AAV ITR's can be modified using standard molecular biology techniques. Accordingly, AAV ITRs used in the vectors of the invention need not have a wild-type nucleotide sequence, and can be altered, e.g., by insertion, deletion or substitution of nucleotides. Additionally, AAV ITRs can be derived from any of several AAV serotypes, including but not limited to, AAV-1, AAV-2, AAV-3, AAV-4, AAV-5, AAV-6, AAVX7, AAV-8 and the like. Furthermore, 5' and 3' ITRs which flank a selected nucleotide sequence in an AAV expression vector need not be identical or derived from the same AAV serotype or isolate, so long as the ITR's function as intended, i.e., to allow for excision and replication of the nucleotide sequence of interest when AAV rep gene products are present in the cell.

The skilled artisan can appreciate that regulatory sequences can often be provided from commonly used promoters derived from viruses such as: polyoma, Adenovirus 2, cytomegalovirus and Simian Virus 40. Use of viral regulatory elements to direct expression of the protein can allow for high level constitutive expression of the protein in a variety of host cells. Ubiquitously expressing promoters can also be used and include, for example, the early cytomegalovirus promoter as described by Boshart et al., Cell, vol. 41, pg. 521, 1985; herpesvirus thymidine kinase (HSV-TK) promoter as described by McKnight et al., Cell, vol. 37, pg. 253, 1984; .beta.-actin promoters, e.g., the human .beta.-actin promoter as described by Ng et al., Mol Cell Biol., vol. 5, pg. 2720, 1985; and colony stimulating factor-1 (CSF-1) promoter and described by Ladner et al., EMBO J., vol. 6, pg. 2693, 1987.

The AAV vector harboring the nucleotide sequence encoding a protein of interest, e.g., chimeric growth factor receptor, and a post-transcriptional regulatory sequence (PRE) flanked by AAV ITRs, can be constructed by directly inserting the nucleotide sequence encoding the protein of interest and the PRE into an AAV genome which has had the major AAV open reading frames ("ORFs") excised therefrom. Other portions of the AAV genome can also be deleted, as long as a sufficient portion of the ITRs remain to allow for replication and packaging functions. These constructs can be designed using techniques well known in the art. (See, e.g., Lebkowski et al. (1988) Molec. Cell. Biol. 8:3988-3996; Vincent et al. (1990) Vaccines 90 (Cold Spring Harbor Laboratory Press); Carter (1992) Current Opinion in Biotechnology 3:533-539; Muzyczka (1992) Current Topics in Microbiol. and Immunol. 158: 97-129; Kotin (1994) Human Gene Therapy 5:793-801; Shelling et al. (1994) Gene Therapy 1:165-169; and Zhou et al. (1994) J. Exp. Med. 179:1867-1875).

Alternatively, AAV ITRs can be excised from the viral genome or from an AAV vector containing the same and fused 5' and 3' of a selected nucleic acid construct that is present in another vector using standard ligation techniques, such as those described in Sambrook et al., Molecular Cloning, a laboratory manual, Cold Spring Harbor Laboratories, N.Y., 1989. Several AAV vectors are available from the American Type Culture Collection ("ATCC").

In order to produce recombinant AAV particles, an AAV vector can be introduced into a suitable host cell using known techniques, such as by transfection. A number of transfection techniques are generally known in the art. See, e.g.; Sambrook et al., Molecular Cloning a laboratory manual, Cold Spring Harbor Laboratories, N.Y., 1989; Davis et al., Basic Methods in Molecular Biology, Elsevier, San Diego, 1986. Particularly suitable transfection methods include calcium phosphate co-precipitation (Graham et al., Virology, vol. 52, pg. 456, 1973), direct micro-injection into cultured cells (Capecchi, Cell, vol. 22, pg. 479, 1980), electroporation (Shigekawa et al., BioTechniques, vol. 6, pg. 742, 1988), liposome mediated gene transfer (Mannino et al., BioTechniques, vol. 6, pg. 682, 1988), lipid-mediated transduction (Feigner et al., Proc. Natl. Acad. Sci. USA, vol. 84, pg. 7413, 1987), and nucleic acid delivery using high-velocity microprojectiles (Klein et al., Nature, vol. 327, pg. 70, 1987).

Suitable host cells for producing recombinant AAV particles include, but are not limited to, microorganisms, yeast cells, insect cells, and mammalian cells, that can be, or have been, used as recipients of a exogenous nucleic acid molecule.

Host cells containing the above-described AAV vectors must be rendered capable of providing AAV helper functions in order to replicate and encapsidate the expression cassette flanked by the AAV ITRs to produce recombinant AAV particles. AAV helper functions are generally AAV-derived coding sequences which can be expressed to provide AAV gene products that, in turn, function in trans for productive AAV replication. AAV helper functions are used herein to complement necessary AAV functions that are missing from the AAV vectors. Thus, AAV helper functions include one, or both of the major AAV open reading frames (ORFs), namely the rep and cap coding regions, or functional homologues thereof.

Alternatively, a vector can be a virus other than the adeno-associated virus, or portion thereof, which allows for expression of a nucleic acid molecule introduced into the viral nucleic acid. For example, replication defective retroviruses, adenoviruses, herpes simplex virus, and lentivirus can be used. Protocols for producing recombinant retroviruses and for infecting cells in vitro or in vivo with such viruses can be found described by Ausubel et al. in Current Protocols in Molecular Biology, Greene Publishing Associates, 1989, Sections 9.10-9.14 and other standard laboratory manuals. Examples of suitable retroviruses include pLJ, pZIP, pWE and pEM which are well known to those skilled in the art. Examples of suitable packaging virus lines include Crip, Cre, 2 and Am. The genome of adenovirus can be manipulated such that it encodes and expresses the protein of interest but is inactivated in terms of its ability to replicate in a normal lytic viral life cycle. See e.g., Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art.

Alternatively, the vector can be delivered using a non-viral delivery system. This includes delivery of the vector to the desired tissues in colloidal dispersion systems that include, for example, macromolecule complexes, nanocapsules, microspheres, beads, and lipid-based systems including oil-in-water emulsions, micelles, mixed micelles, and liposomes. The Puf-A pharmaceutical compositions used for therapeutic administration may be sterilized, as by filtration through sterile filtration membranes (e.g., 0.2 micron membranes). The compositions may be stored in lyophilized form or as a liquid solution. It will be understood that use of certain of the foregoing excipients, carriers, or stabilizers will result in the formation of salts of the Puf-A molecules.

For obtaining a gel formulation, the Puf-A molecule(s) of the composition formulated in a liquid composition may be mixed with an effective amount of a water-soluble polysaccharide or synthetic polymer such as polyethylene glycol to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the Puf-A molecule(s) held within it. Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight polyethylene glycols to obtain the proper viscosity. For example, a mixture of a polyethylene glycol of molecular weight 400-600 with one of molecular weight 1500 would be effective for this purpose when mixed in the proper ratio to obtain a paste.

The compositions of the present invention can also be formulated for administration parenterally by injection. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Carriers, adjuncts or occlusive dressings can be used to increase tissue permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include wetting agents, emulsifying and suspending agents, or sweetening, flavoring, coloring or perfuming agents.

If methylcellulose is employed in the gel, preferably it comprises about 2-5%, more preferably about 3%, of the gel and the Puf-A molecule(s) of the composition is present in an amount of about 300-1000 μg per ml of gel. The dosage to be employed is dependent upon the factors described above. As a general proposition, the Puf-A molecule(s) of the composition is formulated and delivered to the target site or tissue at a dosage capable of establishing in the tissue a maximum dose that is efficacious but not unduly toxic.

Poly(ortho esters) have been introduced into the eye and demonstrated favorable properties for sustained release ocular drug delivery (Einmahl, S., Invest. Opthalmol. Vis. Sci., 43(5), 2002). Polylactide particles have been used to target an agent to the retina and RPE following intravitreous injection of a suspension of such particles (Bourges, J-L, et al, Invest. Opthalmol. Vis. Sci., 44(8), 2003).

In certain embodiments of the invention an ocular implant is so dimensioned and shaped that it fits within the hollow shaft of an injection needle, e.g., a 22, 25, 27, 30, 33, or 35 gauge needle (or needle of any gauge ranging between 22 and 35). Exemplary and nonlimiting dimensions for a cylindrical implant may be about 0.5 to 8 millimeters in length and about 0.1 to 2 millimeters in diameter, e.g., about 0.75 mm to about 1.5 mm in diameter. Implants having other shapes, e.g., other rodlike structures with cross-sections that are rectangular or square in cross-section may have a cross-section in which the two points most distant from each other are separated by at most 0.1 mm to 1 mm. In particular embodiments the intraocular implant may have a length or other longest dimension of between about 5 microns and about 2 mm, or between about 10 microns and about 1 mm for administration with a needle. Alternately, the length or other longest dimension is greater than 1 mm, or greater than 2 mm, such as 3 mm or up to 10 mm. The vitreous chamber in humans is able to accommodate relatively large implants of varying geometries, having lengths of, for example, 1 to 10 mm.

In certain embodiments of the invention the implants may also be at least somewhat flexible, which may facilitate both insertion of the implant in the eye, e.g., in the vitreous, and/or may facilitate accommodation of the implant. The total weight of the implant may be about 250-5000 micrograms, e.g., about 500-1000 micrograms. For example, an implant may weigh about 500 micrograms or about 1000 micrograms. Larger implants may also be formed and further processed before administration to an eye. In addition, larger implants may be desirable where relatively greater amounts of a therapeutic agent are provided in the implant, as used. In various embodiments the ocular implant contains, e.g., between 10 micrograms and 1000 micrograms of an active agent, e.g., between 100 and 500 micrograms, e.g., about 250 micrograms.

The active agent may diffuse out of an implant or may be released as the implant degrades. In one embodiment the sustained release formulation is a biocompatible ocular implant comprising a substantially impermeable polymeric outer layer covering a core which comprises the drug to be delivered, wherein said outer layer has one or more orifices, by which is meant one or more openings in the outer layer through which, when the device is in use, body fluids can enter the device and the drug contained in the device (e.g., dissolved, encapsulated, or entrapped within the device) can migrate out of the device. In certain embodiments the orifices in total have a surface area of less than 10 percent of the total surface area of the device. In certain embodiments of the invention the ocular implant comprises an outer coating layer that is permeable to the therapeutic agent, allowing its slow diffusion out of the implant. The composition, structure, and/or thickness of the coating layer may be selected to provide a particular permeability and diffusion rate.

A drug can be contained in an ocular implant as a dry powder, particles, granules, or as a compressed solid. The drug may also be present as a solution or be dispersed in a polymer matrix. Ocular implants, may be have the active agent or agents homogenously distributed through the polymeric matrix, e.g., they may be monolithic. In other embodiments the active agent(s) are heterogeneously distributed in the polymeric matrix. For example, discrete regions of the implant may contain solid particles of an active agent, or a reservoir of active agent may be encapsulated by the polymeric matrix. The therapeutic agent(s) may be distributed in a non-homogenous pattern in the matrix. For example, an implant may include a portion that has a greater concentration of the therapeutic agent relative to a second portion of the implant. Multilayered structures, with the layers having different compositions and may have different physical characteristics such as density or porosity are another possibility. For example, the layers may contain different therapeutic agents or combinations thereof. In another embodiment, layers that are relatively resistant to degradation are interspersed with layers that degrade more rapidly.

Generally, the dosage needed to provide an effective amount of the composition will vary depending upon such factors as the recipient's age, condition, sex, and extent of disease, if any, and other variables which can be adjusted by one of ordinary skill in the art.

Effective amounts of the compositions of the invention can vary from 0.01-1,000 mg/ml per dose or application, although lesser or greater amounts can be used.

When Puf-A nucleic acid molecules are employed (as in antisense or triplex repression), methods of "gene therapy" are employed. The principles of gene therapy are disclosed by Oldham, R. K. (In: Principles of Biotherapy, Raven Press, NY, 1987), and similar texts. Disclosures of the methods and uses for gene therapy are provided by Boggs, S. S. (Int. J. Cell Clon. 8:80-96 (1990)); Karson, E. M. (Biol. Reprod. 42:39-49 (1990)); Ledley, F. D., In: Biotechnology, A Comprehensive Treatise, volume 7B, Gene Technology, VCH Publishers, Inc. NY, pp 399-458 (1989)); all of which references are incorporated herein by reference. Such gene therapy can be provided to a recipient in order to treat (i.e. suppress, or attenuate) an existing condition, or to provide a prophylactic gene therapy to individuals who, due to inherited genetic mutations, or somatic cell mutation, carry a predisposition to glaucoma.

In some embodiments, viral or retroviral vectors are employed for this purpose of administering Puf-A, its active fragments, derivatives, mimetics and analogs. Examples of suitable vectors are discussed by Fletcher, F. A. et al. (J. Exper. Med. 174:837-845 (1991)), Mkel, T. P. et al. (Gene 118:293-294 (1992)), Porgador, A. et al. (Canc. Res. 52:3679-3686 (1992)), Yoshimura, K. et al. (Nucl. Acids Res. 20:3233-3240 (1992)), Lim, B. et al. (Proc. Natl. Acad. Sci. (U.S.A.) 86:8892-8896 (1989)), Ohi, S. et al. (Gene 89:279-282 1990)), and Russel, S. J. et al. (J. Virol. 66:2821-2828 (1992)).

Examples of appropriate vectors include adenoviral, lentiviral, adeno-associated viral (AAV), poliovirus, HSV, or murine-based viral vectors. Certain embodiments of the present invention use retroviral vector systems. Retroviruses are integrating viruses that infect dividing cells, and their construction is known in the art. Retroviral vectors can be constructed from different types of retrovirus, such as, MoMuLV ("Moloney murine leukemia virus" MSV ("Moloney murine sarcoma virus"), HaSV ("Harvey sarcoma virus"); SNV ("spleen necrosis virus"); RSV ("Rous sarcoma virus") and Friend virus. Lentiviral vector systems may also be used in the practice of the present invention. Retroviral systems and herpes virus system may be particular vehicles for transfection of neuronal cells.

In other embodiments of the present invention, adeno-associated viruses ("AAV") are utilized. The AAV viruses are DNA viruses of relatively small size that integrate, in a stable and site-specific manner, into the genome of the infected cells. They are able to infect a wide spectrum of cells without inducing any effects on cellular growth, morphology or differentiation, and they do not appear to be involved in human pathologies. For example, one may use AAV5 (Davidson et al., Proc. Natl. Acad. Sci. U.S.A., 97: 3428 (2000)); Alisky et al., NeuroReport. 11:2669 (2000)). Methods for preparation of AAV are described in the art, e.g. U.S. Pat. No. 5,677,158. Both adenovirus and adeno-associated virus have been approved for clinical phase I trials.

Intravitreal injections of AAV expressing GDNF have been shown to protect rat retina from ischemia-reperfusion injury by moderate preservation of the inner retina (Wu et al. 2004 Molecular Vision 10, 93-102). Retinal detachment (RD) is a common cause of visual impairment that results in loss of photoreceptors. In an in vivo model, delivery of GDNF using an AAV vector has been shown to protect against RD-induced photoreceptor damage (Wu et al., 2002 IOVS 43, 3480-3488).

Recombinant viruses according to the invention are generally formulated and administered in the form of doses of between about $10^4$ and about $10^{14}$ pfu. In the case of AAVs and adenoviruses, doses of from about $10^6$ to about $10^{11}$ pfu are particularly used. The term pfu ("plaque-forming unit") corresponds to the infective power of a suspension of virions and is determined by infecting an appropriate cell culture and measuring the number of plaques formed. The techniques for determining the pfu titre of a viral solution are well documented in the art.

In the vector construction, the polynucleotide agents of the present invention may be linked to one or more regulatory regions. Selection of the appropriate regulatory region or regions is a routine matter, within the level of ordinary skill in the art. Regulatory regions include promoters, and may include enhancers, suppressors, etc.

Promoters that may be used in the expression vectors of the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda $P_R$, $P_L$, and trp promoters. Among the eukaryotic (including viral) promoters useful for practice of this invention are ubiquitous promoters (for example, HPRT, vimentin, actin, tubulin), intermediate filament promoters (for example, desmin, neurofilaments, keratin, GFAP), therapeutic gene promoters (for example, MDR type, CFTR, factor VIII), tissue-specific promoters (for example, actin promoter in smooth muscle cells, or Flt and Flk promoters active in endothelial cells), including animal transcriptional control regions, which exhibit tissue specificity and have been utilized in transgenic animals: elastase I gene control region which is active in pancreatic acinar cells (Swift, et al. (1984) Cell 38:639-46; Ornitz, et al. (1986) Cold Spring Harbor Symp. Quant. Biol. 50:399-409; MacDonald, (1987) Hepatology 7:425-515); insulin gene control region which is active in pancreatic beta cells (Hanahan, (1985) Nature 315:115-22), immunoglobulin gene control region which is active in lymphoid cells (Grosschedl, et al. (1984) Cell 38:647-58; Adames, et al. (1985) Nature 318: 533-8; Alexander, et al. (1987) Mol. Cell. Biol. 7:1436-44), mouse mammary tumor virus control region which is active in testicular, breast, lymphoid and mast cells (Leder, et al. (1986) Cell 45:485-95), albumin gene control region which is active in liver (Pinkert, et al. (1987) Genes and Devel. 1:268-76), α-fetoprotein gene control region which is active in liver (Krumlauf, et al. (1985) Mol. Cell. Biol., 5:1639-48; Hammer, et al. (1987) Science 235:53-8), α 1-antitrypsin gene control region which is active in the liver (Kelsey, et al. (1987) Genes and Devel., 1: 161-71), beta-globin gene control region which is active in myeloid cells (Mogram, et al. (1985) Nature 315:338-40; Kollias, et al. (1986) Cell 46:89-94), myelin basic protein gene control region which is active in oligodendrocyte cells in the brain (Readhead, et al. (1987) Cell 48:703-12), myosin light chain-2 gene control region which is active in skeletal muscle (Sani, (1985) Nature 314.283-6), and gonadotropic releasing hormone gene control region which is active in the hypothalamus (Mason, et al. (1986) Science 234:1372-8).

Other promoters which may be used in the practice of the invention include promoters which are preferentially activated in dividing cells, promoters which respond to a stimulus (for example, steroid hormone receptor, retinoic acid receptor), tetracycline-regulated transcriptional modulators, cytomegalovirus immediate-early, retroviral LTR, metallothionein, SV-40, E1a, and MLP promoters.

Additional vector systems include the non-viral systems that facilitate introduction of polynucleotide agents into a patient, for example, a DNA vector encoding a desired sequence can be introduced in vivo by lipofection. Synthetic cationic lipids designed to limit the difficulties encountered with liposome-mediated transfection can be used to prepare liposomes for in vivo transfection of a gene encoding a marker (Feigner, et al. (1987) Proc. Natl. Acad. Sci. USA 84:7413-7); see Mackey, et al. (1988) Proc. Natl. Acad. Sci. USA 85:8027-31; Ulmer, et al. (1993) Science 259:1745-8). The use of cationic lipids may promote encapsulation of negatively charged nucleic acids, and also promote fusion with negatively charged cell membranes (Feigner and Ringold, (1989) Nature 337:387-8). Particularly useful lipid compounds and compositions for transfer of nucleic acids are described in International Patent Publications WO 95/18863 and WO 96/17823, and in U.S. Pat. No. 5,459,127. The use of lipofection to introduce exogenous genes into the specific organs in vivo has certain practical advantages and directing transfection to particular cell types would be particularly advantageous in a tissue with cellular heterogeneity, for example, pancreas, liver, kidney, and the brain. Lipids may be chemically coupled to other molecules for the purpose of targeting. Targeted peptides, for example, hormones or neurotransmitters, and proteins, for example, antibodies, or non-peptide molecules could be coupled to liposomes chemically. Other molecules are also useful for facilitating transfection of a nucleic acid in vivo, for example, a cationic oligopeptide (for example, International Patent Publication WO 95/21931), peptides derived from DNA binding proteins (for example, International Patent Publication WO 96/25508), or a cationic polymer (for example, International Patent Publication WO 95/21931).

It is also possible to introduce a DNA vector in vivo as a naked DNA plasmid (see U.S. Pat. Nos. 5,693,622; 5,589,466; and 5,580,859). Naked DNA vectors for therapeutic purposes can be introduced into the desired host cells by methods known in the art, for example, transfection, electroporation, microinjection, transduction, cell fusion, DEAE dextran, calcium phosphate precipitation, use of a gene gun, or use of a DNA vector transporter (see, for example, Wilson, et al. (1992) J. Biol. Chem. 267:963-7; Wu and Wu, (1988) J. Biol. Chem. 263:14621-4; Hartmut, et al. Canadian Patent Application No. 2,012,311, filed Mar. 15, 1990; Williams, et al (1991). Proc. Natl. Acad. Sci. USA 88:2726-30). Receptor-mediated DNA delivery approaches can also be used (Curiel, et al. (1992) Hum. Gene Ther. 3:147-54; Wu and Wu, (1987) J. Biol. Chem. 262:4429-32).

A major problem in the treatment of eye diseases and disorders is the difficulty in delivering biologically active agents into the eye at therapeutically or prophylactically effective concentrations. Oral administration of ocular drugs is mostly inadequate to target the retinal tissues due to the hemato-retinal barriers. In order for an effective amount of a therapeutic agent to reach the ocular area, a high concentration of drug must frequently be administered. This can result in systemic toxicity. For example, pulse therapy may be used to reach high levels of corticosteroids in the eye. Extraocular inserts also have disadvantages. Frequent re-application is necessary because the therapeutic compound dissolves in a matter of hours. Again, these inserts only deliver drug to the cornea and anterior chamber. Topical administration is generally only effective in pathologies involving the superficial surface of the eye, i.e., the cornea and anterior segments. US Patent Application No. 20080183123 discloses methods for of delivering a biologically active agent, in particular a therapeutic or prophylactic nucleic acid, to the ocular sphere of a subject comprising administering said agent to the ciliary body tissue(s) or cells and/or to the extra-ocular muscle tissue or cells.

RNA targets for Puf-A may be identified by any number of methods that detect RNA-protein binding including but not limited to co-immunoprecipitation, microarray analysis and the like. Such techniques are well known in the art and are described by Sambrook, J., E. F. Fritsch, and T. Maniatis (Molecular Cloning: A Laboratory Manual, Cold Spring Harbor Laboratory Press, Cold Spring Harbor, N.Y., (1989)) and Current Protocols in Molecular Biology (F. M. Ausubel et al., eds., John Wiley & Sons. Inc., (1995)).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of the mRNAs that are Targets of Puf-A in Zebrafish

Biotinylated puf-A was prepared from in vitro transcription/translation kit using the TNT Quick coupled reticulocyte lysate system together with the Transcend™ biotinylated lysinetRNA (Promega, Madison, Wis., USA) and then purified through immobilization on streptavidin magnetic beads (Promega) with 5 times PBS wash. Afterwards, the purified biotinylated puf-A were mixed with 10 ug mRNA mixtures from embryos and ovaries. After formaldehyde fix (final 1% concentration), glycine treatment (final 125 mM concentration) and 5 times PBS wash, the residual RNA pulled down by biotinylated puf-A was amplified by using Full Spectrum® Complete Transcriptome RNA Amplification kit (System Biosciences, Mountain View, Calif., USA) as described in the manufacturer's instructions. The PCR products were subcloned into pGEM-T® easy vectors (Promega) and sequenced. Results are shown in Table 2.

Example 2

Identification of HtrA2 as a Target of Puf-A

Computer modeling was used to predict Puf-A as a RNA binding protein. To investigate its target RNA, Flag-mPuf-A was overexpressed in 3T3 cells, and the Flag-mPuf-A with its target RNAs were precipitated by anti-Flag antibody. After proteinase K treatment, the precipitated RNAs were extracted by phenol/chloroform extraction and alcohol precipitation. Then, the RNAs were analyzed by gene expression microarray using GeneChip® Mouse Genome 430 2.0 Array (Affymetrix, California). The results showed that the mRNAs co-precipitated with Puf-A are genes related to cell cycle, neuron development and cell motility. However, one of target RNAs is the IAP binding protein, HtrA2, which is part of apoptosis pathway and is involved in neuron development.

Example 3

Effect of Inhibition of Puf-A Induced Cell Apoptosis and Caspase 3 Activation by siRNA In order to investigate the function of Puf-A, RNAi clones from D19Bwg1357e and human KIAA0020 genes were purchased from National RNAi Core Facility at Academia Sinica. RNAi constructs were transfected to mouse 3T3 cells, and cell apoptosis was analyzed by Annexin® V staining, caspase activation was detected by FLICA™ in vitro Apoptosis Detection Kits (Immunochemistry Technologies, Bloomongton, Minn.). As shown in FIG. 3, siRNA clones for mouse Puf-A gene was transfected to mouse 3T3 fibroblast cells for 3 days. Cells were harvested and stained with Annexin V-FITC (A) or FLICA (B), and were analyzed by flow cytometry. siRNA clone for luciferase gene (Luc siRNA) was used as negative control.

Figure 4:
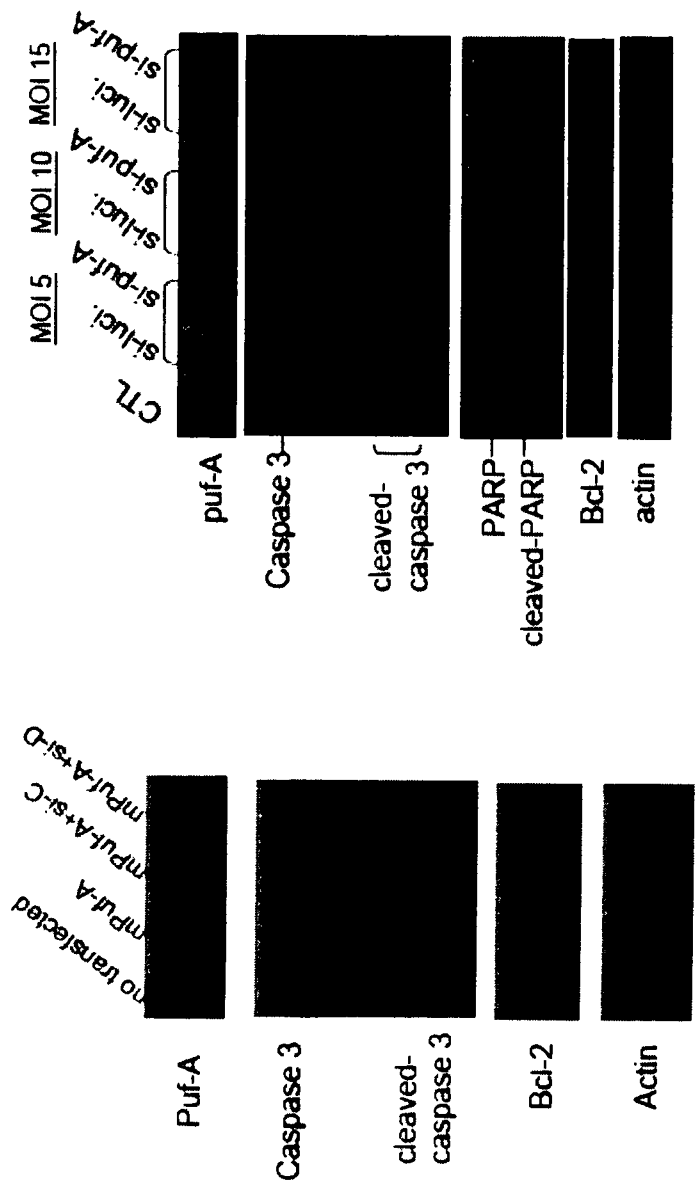
FIG. 4 shows the effect of Puf-A siRNA on induced cell apoptosis and caspase 3 activation in mouse 3T3 and human Be2C cells.

To further study the mechanism of cell apoptosis, RNAi clones were introduced into mouse 3T3 cell and human BE2C cells, the cell lysate was separated by SDS-PAGE following Western blot analysis with Puf-A, caspase 3, Poly (ADP-ribose) polymerase (PARP) and Bcl-2 antibodies. As shown in FIG. 4, mPuf-A and its siRNA clones, si-C and si-D, were co-transfected to mouse 3T3 fibroblast cells (FIG. 4A), and si-Puf-A/lentivirus infected human Be2C cells with MOI 5, 10 or 15 as indicated (FIG. 4B). The cell lysates were analyzed by Western blot with Puf-A, caspase 3, Poly (ADP-ribose) polymerase (PARP) and Bcl-2 antibodies, respectively. It was shown siRNA knocked down Puf-A expression in cells, activated caspase 3, cleaved the caspase 3 substrate PARP, and reduced anti-apoptotic factor, Bcl-2. Actin served as loading control.

Example 4

Inhibition of Puf-A by siRNA

The puf-A siRNA suppressed specifically the zebrafish puf-A expression in 3T3 cell line. The 3T3 cell line was cotransfected with pFlag-puf-A and different siRNAs. In the first line of Western blot, the siRNA was the control siRNA (pcDNA 6.2-GW/EmGFP-miR-neg control plasmid) as negative control. In the middle line, ppuf-A siRNA and in the last line, ppuf-A siRNA containing nanos 39-UTR were used to suppress the puf-A expression. Upper panel showed the Western blot after reaction with anti-Flag antibodies, while lower panel showed Western blot for b-actin as internal control.

Example 5

Expression and cDNA Cloning of the Novel Puf-A Gene in Zebrafish

Figure 5:
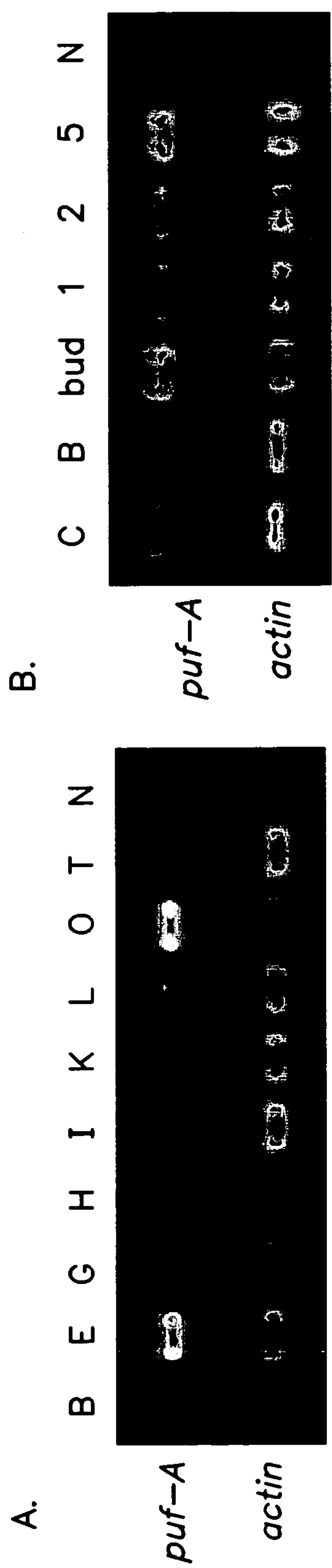
FIG. 5A shows gene expression in adult tissues of zebrafish which were analyzed by RT-PCR and electrophoresis with puf-A primers (upper panel) or actin primers (lower panel, as the internal control). Notation: B, brain; E, eye; G, gill; H, heart; I, intestine; K, head kidney; L, liver; O, ovary; T, testis; N, negative control.
FIG. 5B shows the puf-A gene expressed in various stages of zebrafish embryo. C, cleavage; B, blastula; 1, 1 day post-fertilization (dpf); 2, 2 dpf; 5, 5 dpf; N, negative control.

In zebrafish, using RT-PCR, the puf-A gene was found to be expressed at a high level in the eyes and ovaries. In addition, the puf-A gene was found to a lesser degree in the brain, head kidney (pronephros), and testes (FIG. 5A). This gene was found to be expressed at all stages of zebrafish embryo development (FIG. 5B). In situ hybridization confirmed that puf-A was ubiquitously expressed in zebrafish embryos from fertilization to early somitogenesis. However, it was determined that at a later stage of embryo development, its expression was restricted primarily to the eyes and optic tectum.

In addition, in adult zebrafish ovaries, puf-A was prominently expressed in early immature follicles that were small in size and nested with other developing oocytes. In general, the process of folliculogenesis could be divided into five stages, beginning with the early germline stage I (primary growth) cells that appeared in clusters, through the pre-vitellogenic stage II and the vitellogenic stage III, and ending with the mature or ovulated stages IV and V. Puf-A mRNA expression was noted in primitive stage I ovarian follicles that appeared spherical in shape with diameters less than 100 μm. But this expression declined sharply and became negligible in subsequent stages of oocyte development (e.g. stages II and III). The results of in situ hybridization of ovary cross-sections confirmed that puf-A mRNA expressed prominently in the cytoplasm of stage I follicles which appeared in clusters. In contrast, stage II and III ovarian follicles showed no discernible expression of the puf-A transcript. The expression of puf-A was found to occur when the first wave of follicles begin their process of folliculogenesis.

In Situ Hybridization of Eyes and Ovaries

The collection and staging of embryos were performed as described. Embryos were fixed overnight at 4° C. in 4% paraformaldehyde buffered with 1× phosphate-buffered saline (PFA/PBS). In addition, the ovaries and eyes were removed from zebrafish or mouse after anesthetization and decapitation, and placed in 4% PFA/PBS. After being treated with 30% sucrose, specimens were embedded in OCT. Frozen sections (7 and 10 μm thick for mouse and zebrafish, separately) were collected onto coated slides. In situ hybridization was performed using an InsituPro automated system (Intavis, Koeln, Germany). Whole-mount and section in situ hybridization were carried out using a digoxigenin (DIG)-labeled RNA probe and anti-DIG antibody conjugated with alkaline phosphatase as described previously. After hybridization, slides were incubated with anti-DIG antibody conjugated with AP, and developed with NBT-BCIP reagents. The in situ hybridization analysis of the cryosections of adult zebrafish eyes was carried out with a zebrafish puf-A riboprobe after fluorescein (Flu) labeling. After hybridization, slides were incubated with anti-Flu-AP, and developed with FastRed reagents.

The following DIG-labeled RNA probes were prepared from linearized plasmids using the DIG RNA labeling kit (Roche, Basel, Switzerland): (1) an antisense probe of the puf-A gene prepared from KpnI-digested pBluescript SK-puf-A (full-length, 2,053 bp) using T3 RNA polymerase, (2) a puf-A sense probe prepared from BamHI-digested pBluescript SK-puf-A using T7 RNA polymerase, and (3) a vasa antisense probe prepared from XbaI-digested pBluescript SK-vasa (a gift from Dr. Bon-chu Chung, Academia Sinica) with T7 RNA polymerase. Follicles at different stages of development were identified according to the different-sized diameters of the follicles.

Example 6

Phylogenetic Relationships of Puf-A-Related Proteins

A search for Puf-A-related sequence fragments in the databases suggested that the Puf-A in zebrafish is a member of the Puf family. Each Puf protein contains a Puf domain that consists of several tandem Puf repeats of 36 amino acids. The Puf domain has also been known as the pumilio homolog domain. In total, 14 Puf-related proteins of zebrafish, mouse, and human were identified using the SMART server (Table 1). A phylogenetic tree constructed using the PHYLIP package indicates that these 14 Puf proteins can be grouped into three clusters: (1) the Puf-A homolog cluster, (2) the C14orf21 homolog cluster, and (3) the PUM1/PUM2 homolog cluster.

Sequence similarities among these Puf proteins in each cluster were analyzed and categorized. In this study, the human and mouse Puf-A homologs, i.e., KIAA0020 and D19Bwg1357e in Table 1, are designated, respectively, as the human and murine Puf-A, respectively. BLASTP analysis revealed that human Puf-A shared 89% identity in the aligned 647 amino acid residues with murine Puf-A and 66% identity with zebrafish Puf-A in the aligned 621 residues. However, compared with human related proteins in the other two categories, human Puf-A and human C14orf21 showed no significant similarity and human Puf-A and Pumilio (PUM1) shared only 21% identity in the aligned 241 amino acid residues (Table 1). Similarly, human Puf-A and human PUM2 shared only 20% identity in the aligned 240 residues. Thus, members of the Puf-A cluster are similar to each other, but distinct from the members of the other two clusters. Based on the results of the phylogenetic and sequence similarity analyses, Puf-A homologs could be grouped into a single cluster.

On the other hand, within the cluster of C14orf21 homologs, human C14orf21 showed 84% identity with murine 2610027L16Rik in the aligned 581 residues and 34% identity with zebrafish L00564287 in the aligned 619 residues. However, human C14orf21 showed no significant similarity with human Pumilio (PUM1), and human C14orf21 and human PUM2 shared only 23% identity in the aligned 140 amino acid residues. Thus, C14orf21 homologs could be grouped into a single cluster.

As to the cluster of PUM1/PUM2 homologs, human Pumilio (PUM1) and PUM2 shared 75% identity in the aligned 1,076 residues and human and mouse Pumilio (PUM1) shared 98% identity in the aligned 1,189 residues. In zebrafish, there were four Puf proteins in this cluster (Table 1) and their similarity analyses were described in Data S1. The results described above support the clustering of the homologs of PUM1 and PUM2 into one group in our phylogenetic tree analysis.

Phylogenetic Analysis

A multiple-sequence alignment for these Puf-related protein sequences was generated by CLUSTAL X2.0, using the BLOSUM series matrix. The option for a negative matrix was turned on, while the other parameters remained at the default setting. The BLASTP algorithm with the BLOSUM62 matrix, which was implemented in BLAST at NCBI, was used for the sequence similarity analysis. A phylogenetic tree of putative Puf proteins was constructed using algorithms with PHYLIP vers. 3.67. The final unrooted tree diagram was prepared using DENDROSCOPE vers. 1.2.4.

Example 7

Computer Modeling of Human Puf-A

Based on the crystal 3D structure of the human Pumilio domain with 1.9 A resolution, a computer modeling of the Puf-domain for human Puf-A (KIAA0020) was conducted using its 336 amino acid residues from Asp-151 to Ile-486. The quality of this modeling evaluated by the VADAR server showed that 100% of the residues were in the allowed regions of the Ramachandran diagram.

The computer model of human Puf-A predicted its structure to be composed of six Puf repeats, each of which constitutes a unique superhelix, half doughnut-shaped Puf domain. The six Puf repeats are distributed in two separate regions from Leu-165 to Glu-273, and from Ala-350 to Glu-460. These six repeats are structurally aligned with corresponding repeats of the template used in this computer modeling. Moreover, each repeat has three helices and the second helix, which is located at the inner, concave face of the model, and interacts with RNA exhibiting characteristic features of a conventional Puf repeat.

On the other hand, the sequence from Glu-274 to Glu-349, which represents the middle region of this model contains no typical Puf repeats identifiable by the SMART server. Detailed analysis of this model showed that this middle region possesses a length of segment close to two tandem Puf repeats (76 residues) and each of these “repeat-like” structures exhibits features of three-helix similar to a typical Puf repeat. It is concluded that this middle region mimics two Puf repeats structurally. Thus, the overall structure of Puf-A features a six-Puf-repeat domain with an intermediate region of two repeat-like segments so that it displays a topology similar to the conventional eight-repeat Pumilio homolog domain. Furthermore, this computer model of human Puf-A demonstrates that it is a new RNA-binding protein, distinctly different from the Pumilio domain.

In addition, the values of electrostatic potentials on the molecular surface of this model of human Puf-A were calculated. An asymmetric distribution of electrostatic potentials was noted for the Puf domain of Puf-A: its concave surface has predominately positive basic electrostatic potentials, presumably for RNA binding, while the convex surface in this model is acidic with partly hydrophobic areas. Similar properties of the electrostatic surface of this model were also observed in the crystal structure of Pumilio.

Modeling the Puf Domain of Human Puf-A (KIAA0020)

In order to model the three-dimensional (3D) structure of human Puf-A, the mGenTHREADER method of the PSIPRED server was used for predicting secondary structures and making sequence alignments. Initially, the structural information of human Pumilio homolog domain (Protein Date Bank code: 1IB2 and 1M8Y) was used as modeling templates. Even though the sequences of human Pumilio (PUM1) is only 21% identity with human Puf-A, the crystal structure of Pumilio homolog domain is similar to Puf-A detected by mGenTHREADER with p value<0.0001.

Then 3D structure of Puf domain in human Puf-A was constructed by MODELLER 9v3. A segment of the RNA ligand from 1M8Y was assembled into the resulting model to represent the potential RNA binding site. Furthermore, the electrostatic potentials were calculated using DELPHI with default parameters setting in CHIMERA. The color spectrum mapped onto the domain surface ranged from −7 kT/e (dark red) to +7 kT/e (dark blue). Finally, 3D structural diagrams in this study were prepared using CHIMERA. The convex and concave surfaces represent the presentation of the model that had been rotated 180° about the vertical axis.

Example 8

Eye Defects in the MO Knockdown of the Puf-A Gene

Figure 6:
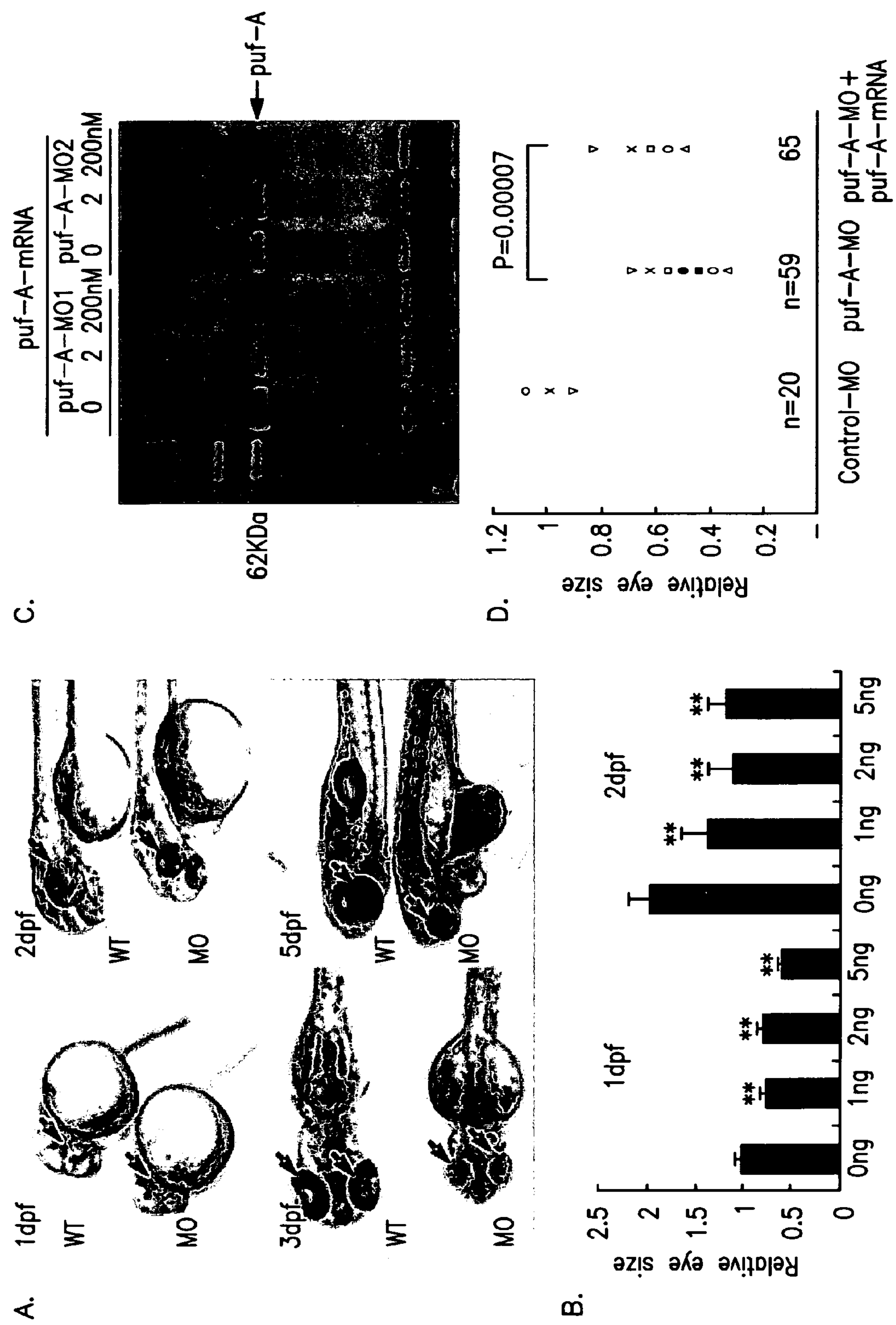
FIG. 6A shows Zebrafish embryos at the 1~4-cell stage were treated with 5 ng puf-A morpholino (MO1) by microinjection. The phenotypes of the wild-type and morphants are shown in lateral view at 1, 2, 3, and 5 days post-fertilization (dpf) after treatment. Black arrows point to the eyes.
FIG. 6B shows various amounts of MO1 were microinjected into zebrafish embryos, and the eye size was measured at 1 or 2 dpf and compared to the eye size of control fish. The "relative eye size" was defined by the value of eye size in MOs relative to the average size of eyes in normal embryos of WT fish. The average value of eye size in normal embryos at 1 dpf was considered as 1. Error bars represent the standard error of the mean. **refer to $p<0.01$ Student's t-test).
FIG. 6C shows MO1 or puf-A-MO2 when added to puf-A generated through in vitro transcription/translation reactions. One microliter of the reaction mixture was separated on 10% SDS/PAGE, blotted, incubated with streptavidin-AP, and developed with NBT-BCIP reagents.
FIG. 6D shows the 5 ng control- or puf-A-MO1 was used for microinjection. In addition, 200 pg of capped puf-A RNA was co-injected with puf-A-MO1 to check the specificity of MO knockdown. The "relative eye size" was defined as above. The eye size was measured at 2 dpf. Control-MO, n=20 embryos; puf-A-MO1, n=59; puf-A-MO1+ capped RNA, n=65. The p value in Student's t-test for the difference between puf-A-MO and puf-A-MO+mRNA was <0.00007.

To examine the biological function of the puf-A gene, zebrafish embryos at the 1~4 cell stage were injected with one of the two puf-A-MO antisense oligonucleotides, MO1 and MO2. As illustrated in FIG. 6A, MO1 morphants clearly showed small eyes, a small head, and brain edema at 1 and 2 dpf. Relative to the eye size of WT fish, there were significant reductions in eye size among the morphants in a dose-responsive manner (~40% reduction with 5 ng puf-A-MO1; FIG. 6B). The puf-A-MO2 gave results similar to those of the puf-A-MO1.

In order to further demonstrate the efficiency of MO1 and MO2, in vitro transcription/translation of puf-A was performed in the presence or absence of 0~200 nM MOs. It was shown that these MOs blocked puf-A translation in vitro, especially at high concentration (FIG. 6C). The specificity was further confirmed by the experiment in which the addition of capped puf-A RNA partially but significantly rescued the phenotype of eye size in MO-induced morphants in vivo (p value<0.00007; FIG. 6D).

Furthermore, in order to circumvent the potential issue of “off-target effects” of MOs, not only a wide range of MOs (1 to 10 ng/embryos) was used for gene knockdown experiments, but also a 5 bp mismatch puf-A (5 mmMO1) was employed as a negative control for MO1. Both in vitro and in vivo analyses were performed to examine the specificity for MOs. First, the addition of various amounts (0, 2, and 200 nM) of the puf-A-5 mmMO1 did not affect the transcription/translation reactions for puf-A in vitro. Secondly, for in vivo experiment, the puf-A 5'-UTR and its partial coding region were added onto pEYFP-N1 plasmid which contained CMV promoter and YFP gene to generate the ppuf-A-YFP plasmid. In vivo, approximately 31.2% of embryos injected with this ppuf-A-YFP exhibited fluorescence at 100 pg/embryo dosage.

However, co-injection with MO1 totally suppressed the YFP expression; in contrast, the mismatch control, 5 mmMO1, did not affect the YFP expression. It is further noted that the phenotypes of morphants injected with 5 mmMO1 were also normal at 3 dpf, similar to WT zebrafish.

Furthermore, an independent approach using various siRNAs was performed in order to validate the MO data. The puf-A siRNA (i.e. without nanos 3'-UTR) was shown to suppress the zebrafish puf-A expression and generate a reduction in the eye size of zebrafish embryos after microinjection as compared with eye size when injected with control siRNA 2 dpf. Therefore, both MOs and siRNA knockdown analyses indicate that these genetic tools specifically knocked down the expression of puf-A leading to eye defects in zebrafish.

In situ markers, such as emx3 (telencephalon marker), krcx20 (rhombomere 3/5 marker), pax6a (forebrain, retina, hindbrain, spinal cord marker), mab2111 (retina, optic tectum and hindbrain marker), mab2112 (retina, optic tectum and hindbrain marker), rx3 (retina marker), six3b (retina/diencephalon/midbrain marker) etc were used to characterize the eye defects during embryo development. In situ hybridization showed that most brain regions were normal at 1 dpf, but some regions (like optic tectum and eyes) developed abnormal defects that occurred at 2 dpf. For example, six3b expressed only in ganglion cell layer of eye tissues in wild type 2 dpf; but this gene expressed all over in eye tissue in morphants. Furthermore, expression of another marker, mab2111, was found in retina, optic tectum and hindbrain. In contrast, in morphants, no mab2111 expression was found in the entire eye tissue or optic tectum.

Puf-A knockdown promoted apoptosis in eye tissues at 1 dpf as compared to control. It seemed that cell death occurred prior to retinal differentiation which occurred approximately 28-30 hpf. Moreover, the other retinal differentiation markers (ath5/atoh7) were not expressed in morphants as late as 36 hpf in in situ experiments (pictures not shown), suggesting that the puf-A knockdown led to specific differentiation defects in eyes, not simply delayed development.

Subsequently, at the development stages of 3 and 5 dpf, eye sections of WT fish and morphants were further examined. In WT zebrafish, the retina comprises several layers of differentiated cells including retinal ganglion cells, the inner plexiform layer, amacrine cells, bipolars, outer plexiform layer, rods and cones, and pigmented cells. In contrast, morphants with puf-A gene knockdown exhibited features of an undifferentiated retina with loss of detailed architecture and a significant reduction in eye size. Structures such as the rod and cone layers were not concentrically organized and retinal ganglion cells and plexiform layers were not readily discernible.

Morpholino (MO) Knockdown

Zebrafish embryos were obtained by natural mating and MO microinjection was performed at the stage of 1~4 cells. The puf-A-MO1 antisense oligonucleotide 5'-AATGGACCATGTGTACAGACAAACA-3' was designed to direct against the 5' UTR of the puf-A gene, and the puf-A-MO2 antisense oligonucleotide was 5'-TTTACCCTCCATAATGGACCATGTG-3' that directed against the 5' UTR and part of coding region including ATG. The 5 bp mismatch MO1 as a negative control for MO (i.e. puf-A 5 mmMO1) was 5'-AATcGACgATGTGTAgAcACAAAgA-3'. Embryos positioned in an agarose injection chamber were injected with 5~10 ng of MO in 4.6 nl using a Narishige micromanipulator and needle holder (Narishige, Tokyo, Japan). For the experiment, eye size was determined by photographing lateral views of anesthetized larvae and was normalized to the average eye size of age-matched WT fish.

In Vitro Transcription/Translation

An in vitro transcription/translation assay was carried out with the TNT Quick coupled reticulocyte lysate system together with the Transcend™ biotinylated lysine-tRNA (Promega), according to the manufacturer's protocol. MOs were added to the complete TNT Quick Master Mix to final concentrations of 0.1 or 10 μM and incubated at 30° C. for 90 min. One microliter of this reaction mixture was resolved on 10% SDS/PAGE, and biotin-labeled lysine residues were detected on Western blots via a streptavidin-alkaline phosphatase and visualized with NBT-BCIP reagents.

Rescue Experiment of Morphants

Rescue experiments were performed by injecting the synthesized capped puf-A RNA with puf-A-MO1. The capped puf-A RNA that did not contain a 5' UTR region was prepared from a pBluescript SK-plasmid after BamHI digestion using the mMessage mMachine kit (Ambion, Austin, Tex., USA). For the rescue experiments, 200 pg of capped puf-A RNA was microinjected with puf-A-MO1 into zebrafish embryos, and the eye size was measured at 2 dpf.

Puf-A Silencing in the Zebrafish PGCs

To silence the puf-A expression in zebrafish with small interfering RNA (siRNA), the pcDNA6.2-GW/EmGFP-miR (Block-iT Pol II miR RNAi Expression Vector Kits, Invitrogen) was used to construct the puf-A siRNA plasmid according to the user manual. The region of nt1078 to 1098 for zebrafish puf-A was chosen for the engineered puf-A siRNA plasmid. The commercial pcDNA 6.2-GW/EmGFP-miR-neg control plasmid served as the "control siRNA". In addition, the 3' UTR fragment of nanos prepared from the PCR product of pGEM-T Easy-nanos plasmid (a gift from Dr. Bon-chu Chung) was subcloned into XhoI site of the puf-A siRNA and control siRNA plasmids, separately, to generate the plasmid with either puf-A siRNA or control siRNA containing nanos 3' UTR. Therefore, there are four siRNA plamids: puf-A siRNA with or without nanos 3' UTR and their two respective control plamids without puf-A.

Then, the PCR products generated from these four siRNA plasmids using forward primer (ACAAGTTTGTACAAAAAAGCAGGCT) and reverse primer (ACCACTTTGTACAAGAAAGCTGGGT), were subcloned into pGEM-T Easy vector using a TA cloning kit (Promega). Afterwards, using the mMessage mMachine kit (Ambion), the RNAs with puf-A containing either or no nanos 3' UTR and their controls without puf-A were prepared separately. Finally, 100-200 pg of these puf-A siRNAs and control siRNAs (with or without nanos 3' UTR) was microinjected into one-cell stage of zebrafish embryos, and the phenotypes and vasa expression were observed under microscope.

Example 9

Defects of Primordial Germ-Cell Development in the MO and siRNA Knockdown

During embryo development, primordial germ cells (PGC) follow a unique developmental path that is characterized by specification and migration of these cells to colonize the gonads where they differentiate into gametes. To investigate whether puf-A is involved in PGC development, the puf-A MO from above was used to knockdown its expression in the early stage of zebrafish embryos. In situ hybridization with zebrafish PGC-specific vasa RNA was employed as a marker to monitor PGCs migration. It has been reported that zebrafish PGC movement began with four random clusters before 6 hpf to form two clusters that would move to either side of embryo midline by the end of the first day of development. PGCs appeared in gonad regions as two clusters in WT embryos at the 16~20 hpf stage, but the morphants exhibited prominent abnormalities at the same stage of development with either a reduction in PGC numbers (50.4%) or abnormal patterns of migration (34.4%) indicating the failure of PGC navigation towards their destined sites.

Since MO knockdown could affect various tissues in embryos, it remained unclear whether the abnormal patterns of PGC migrations were caused directly by specific knockdown of puf-A expression in PGCs. It was reported that the 3' UTR of nanos plays critical roles in RNA stabilization and could assure specific expression of reporter gene in PGC regions. Herein, a puf-A siRNA prepared with nanos 3' UTR was microinjected into embryos. These embryos showed normal size head and eyes up to 2 dpf but they already displayed a marked reduction in PGC numbers (80.9%) and abnormal patterns of migration (11.3%) at 16 hpf of development. In contrast, the puf-A siRNA (without nanos 3' UTR) had the similar phenotypes as MO morphants with small eyes, small head, and brain edema in addition to abnormal PGC migration and reduction in PGC number. Furthermore, the control siRNA with nanos 3'-UTR exhibited normal PGC migration and normal eye size development. Thus, specific knockdown of puf-A in PGCs led to abnormal PGC development in zebrafish embryo.

Example 10

Expression of the Puf-A Gene in Eye Tissues of Adult Mice

The puf-A gene was identified in the mouse genome as the mouse D19Bwg1357e (Table 1). As puf-A MO knockdown led to abnormal differentiation in zebrafish eye, puf-A expression in mouse eyes was investigated. The in situ hybridization analysis showed that puf-A was expressed in retina ganglion cells of mice, and to a lesser degree, in the pigmented cells of mice as well (see arrows in FIG. 5), suggesting that the Puf-A protein may play an important role in the function of vertebrate eyes.

Paraffin Embedding and Sectioning of Mouse

Eyes from mouse were collected and placed in 4% paraformaldehyde. Tissue sections (3 μm thick) from paraffin-embedded tissue blocks were placed on charged slides, deparaffinized in xylene, rehydrated through graded alcohol solutions and stained with hematoxylin and eosin (H&E).

Example 11

Identification of the mRNA Targets for Puf-A in Zebrafish

The biotinylated puf-A was prepared from in vitro transcription/translation) and then purified through immobilization on streptavidin magnetic beads. Afterwards, the purified biotinylated puf-A were mixed with 10 ug mRNA mixtures from embryos and ovaries. After fix and PBS wash, the residual RNA pulled down by biotinylated Puf-A was amplified, subcloned and sequenced. Using this pull-down assay, many potential RNA targets for puf-A bindings were found and listed in Table 2 with their gene IDs and symbols. We further showed that there was a reciprocal relationship for the expression of puf-A and one of its potential RNA targets, prdm1a. (Jui-Chin Chang and John Yu, unpublished observations). Therefore, these results and computer modeling predicted that puf-A is a RNA binding protein.

Briefly, biotinylated puf-A was prepared from in vitro transcription/translation kit using the TNT Quick coupled reticulocyte lysate system together with the Transcend™ biotinylated lysine-tRNA (Promega, Madison, Wis., USA) and then purified through immobilization on streptavidin magnetic beads (Promega) with 5 times PBS wash. Afterwards, the purified biotinylated puf-A were mixed with 10 ug mRNA mixtures from embryos and ovaries. After formaldehyde fix (final 1% concentration), glycine treatment (final 125 mM concentration) and 5 times PBS wash, the residual RNA pulled down by biotinylated puf-A was amplified by using Full Spectrum Complete Transcriptome RNA Amplification kit (System Biosciences, Mountain View, Calif., USA) as described in the manufacturer's instructions. The PCR products were subcloned into pGEM-T easy vectors (Promega) and sequenced.

Example 12

Puf-A Relationship to Blimp-1

It was further demonstrated that biotinylated puf-A was able to pull down Blimp-1 mRNA specifically from an RNA pool after RT-PCR and TA cloning. This interaction demonstrates that Blimp-1 mRNA is a downstream target of puf-A which may serve as a mechanism for regulating Blimp-1. Blimp-1 has been shown to be a regulator of the specification of germ cell lineage.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

We claim:

1. A method for expressing a Puf-A gene in an ocular cell, the method comprising:

providing at least a portion of a Puf-A gene suitable for expression of a Puf-A therapeutic protein;

incorporating the gene into a vector;

transfecting the vector into at least one ocular cell; and expressing at least the portion of the therapeutic Puf-A protein in the at least one ocular cell.

2. The method of claim 1, wherein the ocular cell is from a human or animal subject having a retinal disease selected from the group consisting of progressive ganglion cell degeneration, retinitis pigmentosa, retinal ischemia, Leber's hereditary optic neuropathy, age-related macular degeneration, diabetic retinopathy, open angle glaucoma, and glaucoma.

3. The method of claim 1, wherein the vector is a viral vector selected from the group consisting of adeno-associated viral vector, adenoviral vector, retroviral vector, herpes viral vector, parvoviral vector, and lentiviral vector.

4. The method of claim 1, comprising: transfecting at least one of human retinal cell or retinal progenitor cells with the vector.

5. The method of claim 3, further comprising:

providing a recombinant adeno-associated virus (AAV) carrying a nucleic acid sequence encoding the normal Puf-A gene product, an active polypeptide fragment thereof, an analog thereof or a peptidomimetic thereof, under the control of a promoter sequence which expresses the product of the gene in the ocular cells;

administering to the subject by a subretinal, intravitreal, topical, subconjunctival, retrobulbar, periocular, suprachoroidal, or intraocular route an amount of the recombinant AAV sufficient to express an effective amount of the normal Puf-A gene product, an active polypeptide fragment thereof, an analog thereof or a peptidomimetic thereof in the ocular cells and thereby treating the retinal disease.

6. The method of claim 5 wherein the human or animal subject is characterized by a defect or absence of a normal Puf-A gene in ocular cells.

7. The method of claim 5, wherein the AAV vector infects ganglion and photoreceptor cells with high efficiency.

8. The method of claim 5, wherein the promoters are cell-specific promoters.

9. The method of claim 5, wherein expression of the normal Puf-A gene product, an active polypeptide fragment thereof, an analog thereof or a peptidomimetic thereof in an ocular cell of a subject, binds an RNA corresponding to a gene selected from the group consisting of zgc:193933, prdmla, spata2, texlO, rbb4, ddx3, zp2.2 and HtrA2 RNA.

10. The method of claim 5, wherein the AAV is a recombinant AAV having a cap-region from AAV type (1) and a rep-region from AAV type (2).

11. The method of claim 1, wherein the vector is a non-viral vector.

12. The method of claim 11, wherein the non-viral vector is a liposome-mediated delivery vector.

13. The method of claim 1, wherein the retinal disease is caused by a mutation in the normal Puf-A gene.

14. The method of claim 1, wherein the retinal disease is caused by overexpression or hyperactivity of a binding target of the normal Puf-A gene product.

15. The method of claim 14, wherein the binding target of the Puf-A gene product is selected from the group consisting of zgc:193933, prdmla, spata2, texlO, rbb4, ddx3, zp2.2 and HtrA2.

16. The method of claim 1, wherein the vector is suitable for delivery to a mammal by ocular injection, intravitreolar injection, retinal injection, or subretinal injection.

17. The method of claim 14, wherein binding of the Puf-A gene product to the binding target inhibits a gene involved in apoptosis.

18. The method of claim 17, wherein the target gene is caspase 3.

* * * * *

SEQUENCE LISTING

```
<160> NUMBER OF SEQ ID NOS: 4

<210> SEQ ID NO 1
<211> LENGTH: 2053
<212> TYPE: DNA
<213> ORGANISM: Danio rerio
```

<400> SEQUENCE: 1

```
ccgtaaagtt gtttgtctgt acacatggtc cattatggag ggtaaaccaa gaaagaaatc     60
attcactcca agagacggaa agaaaccttc attcaaatcc aaaggtaaac ctggaggaaa    120
accacaaggc aaacggccat tcaaacctca caacaatgac aaaggcaaag gttttagaaa    180
gtcaggtgga gaaggaggac cacagaagtt caacagaaaa ccaacagatg gaaaatttgc    240
caagaagaga aaatttcctg gagacagaat caaacaagag gaaggtgctg agcgaaaaaa    300
acctaaatgg gatgagttta aacaaaaaaa gaaagaactg aagctgaatc gtcagcagac    360
tgatagaaaa gagagctacc agatcgtaag cagagcaaag caagtgtggg agatggtaag    420
acggaaagac tgtgataagc aaaaaaggac taaactgatg aaagagctgc aggatcttgt    480
aaaaggcaaa attaaaacga ttgcatttgc gcatgattcc acgcgggtgc ttcagtgttt    540
tattcaattt ggcagtgata agcagagaaa ggaggtgttt gatgaactca aagaacacat    600
tgtggagttg agtaaatcaa aatatgccag aaacattgta aagaagttcc taatgtatgg    660
gagtaaagag caggtaggtg aagtgatgtt ggcttttaaa gggaaagtca ggcagatgct    720
cagacactcg gaggcgtctt cagttgtgga atacgcttat aatgataaag ccatcctctc    780
tcagagactc atgctcactg aggagctcta cggaaacacg ttcaccgtct taaagtcatc    840
agtttgtcct acgttagaga aagttcttga agcaaatcca gggaaattgg agagcatctt    900
ggatgaaatg aagcagatcc ttacacccat ggcacagaaa gaggctgtca ttaaacattc    960
attggttcac aaagttttcc tggacttctt tgagcacgct ccggacaaac agagaacgga   1020
gatgattgag tcgatcagag aggccgtcgt gtacatggca cacacacacg atggagccag   1080
agtcaccatg cactgtttat ggcacggcac aactaaggac cgaaaggtta tagtaaaaac   1140
gatgaaatcg tatattgcaa agtttgccat gggtgaatat gctcatcttg tacttttggc   1200
tgcattcgat tgcattgatg acaccaagct ggttaaacaa attattatct cagaaatggt   1260
tagttcctta tctgaaataa tcagcaataa acacggtaaa aaggtgctgc tttacctgct   1320
gagtcctaga gaccctgctc acctcttacc tgaaatcatt caagtgctgg agaaagggga   1380
tggcaatgcg cacagtaaga aggatgtgct gatcaggaga aaggagctgc tggaggccgc   1440
gtctccttct ctgctgaatc atctgtgtga aaacgctcag tctatggtca tggataaatc   1500
ctgctgtgtg gtggtgagcg acatactggg ctctgctgtt ggagatctca gacctgctat   1560
ggaggcagtg gcagctctgg cagatggacc ccttatacca ggtggaaagg atggacagct   1620
gcatatggct gaacaccccg ctggtcatct ggtgctgaaa tggttgatcg agcaggacac   1680
caagatgaag gacacagaga gagaggagcg tttttccagg attcttctgg agaaggttgg   1740
gttggagaac ctcaagacat gggcttcggt caaccgtggt gccattattc tttgttgtct   1800
tctccagagc gcagatgaaa gtgttgctga agaagtgaaa gctatgctga aatccagcat   1860
tcctgagcta cagcggctcc agaactcaaa aggaattgag gttctgcttg aaaaacttgc   1920
ataaaaagtt cgatctatca atgatttttc tttgttttct ccagtttttt taaaattgtg   1980
catttctatg atgttgtatg taaatacaaa ttacacacaa tgagacctgg aaaaaaaaaa   2040
aaaaaaaaaa aaa                                                      2053
```

<210> SEQ ID NO 2
<211> LENGTH: 629
<212> TYPE: PRT
<213> ORGANISM: Danio rerio

```
<400> SEQUENCE: 2

Met Glu Gly Lys Pro Arg Lys Lys Ser Phe Thr Pro Arg Asp Gly Lys
1               5                   10                  15

Lys Pro Ser Phe Lys Ser Lys Gly Lys Pro Gly Gly Lys Pro Gln Gly
            20                  25                  30

Lys Arg Pro Phe Lys Pro His Asn Asn Asp Lys Gly Lys Gly Phe Arg
        35                  40                  45

Lys Ser Gly Gly Glu Gly Gly Pro Gln Lys Phe Asn Arg Lys Pro Thr
    50                  55                  60

Asp Gly Lys Phe Ala Lys Lys Arg Lys Phe Pro Gly Asp Arg Ile Lys
65                  70                  75                  80

Gln Glu Glu Gly Ala Glu Arg Lys Lys Pro Lys Trp Asp Glu Phe Lys
                85                  90                  95

Gln Lys Lys Lys Glu Leu Lys Leu Asn Arg Gln Gln Thr Asp Arg Lys
            100                 105                 110

Glu Ser Tyr Gln Ile Val Ser Arg Ala Lys Gln Val Trp Glu Met Val
        115                 120                 125

Arg Arg Lys Asp Cys Asp Lys Gln Lys Arg Thr Lys Leu Met Lys Glu
    130                 135                 140

Leu Gln Asp Leu Val Lys Gly Lys Ile Lys Thr Ile Ala Phe Ala His
145                 150                 155                 160

Asp Ser Thr Arg Val Leu Gln Cys Phe Ile Gln Phe Gly Ser Asp Lys
                165                 170                 175

Gln Arg Lys Glu Val Phe Asp Glu Leu Lys Glu His Ile Val Glu Leu
            180                 185                 190

Ser Lys Ser Lys Tyr Ala Arg Asn Ile Val Lys Lys Phe Leu Met Tyr
        195                 200                 205

Gly Ser Lys Glu Gln Val Gly Glu Val Met Leu Ala Phe Lys Gly Lys
    210                 215                 220

Val Arg Gln Met Leu Arg His Ser Glu Ala Ser Ser Val Val Glu Tyr
225                 230                 235                 240

Ala Tyr Asn Asp Lys Ala Ile Leu Ser Gln Arg Leu Met Leu Thr Glu
                245                 250                 255

Glu Leu Tyr Gly Asn Thr Phe Thr Val Leu Lys Ser Ser Val Cys Pro
            260                 265                 270

Thr Leu Glu Lys Val Leu Glu Ala Asn Pro Gly Lys Leu Glu Ser Ile
        275                 280                 285

Leu Asp Glu Met Lys Gln Ile Leu Thr Pro Met Ala Gln Lys Glu Ala
    290                 295                 300

Val Ile Lys His Ser Leu Val His Lys Val Phe Leu Asp Phe Phe Glu
305                 310                 315                 320

His Ala Pro Asp Lys Gln Arg Thr Glu Met Ile Glu Ser Ile Arg Glu
                325                 330                 335

Ala Val Val Tyr Met Ala His Thr His Asp Gly Ala Arg Val Thr Met
            340                 345                 350

His Cys Leu Trp His Gly Thr Thr Lys Asp Arg Lys Val Ile Val Lys
        355                 360                 365

Thr Met Lys Ser Tyr Ile Ala Lys Phe Ala Met Gly Glu Tyr Ala His
    370                 375                 380

Leu Val Leu Leu Ala Ala Phe Asp Cys Ile Asp Asp Thr Lys Leu Val
385                 390                 395                 400

Lys Gln Ile Ile Ile Ser Glu Met Val Ser Ser Leu Ser Glu Ile Ile
                405                 410                 415
```

```
Ser Asn Lys His Gly Lys Lys Val Leu Leu Tyr Leu Leu Ser Pro Arg
            420                 425                 430

Asp Pro Ala His Leu Leu Pro Glu Ile Ile Gln Val Leu Glu Lys Gly
        435                 440                 445

Asp Gly Asn Ala His Ser Lys Lys Asp Val Leu Ile Arg Arg Lys Glu
    450                 455                 460

Leu Leu Glu Ala Ala Ser Pro Ser Leu Leu Asn His Leu Cys Glu Asn
465                 470                 475                 480

Ala Gln Ser Met Val Met Asp Lys Ser Cys Cys Val Val Val Ser Asp
                485                 490                 495

Ile Leu Gly Ser Ala Val Gly Asp Leu Arg Pro Ala Met Glu Ala Val
            500                 505                 510

Ala Ala Leu Ala Asp Gly Pro Leu Ile Pro Gly Gly Lys Asp Gly Gln
        515                 520                 525

Leu His Met Ala Glu His Pro Ala Gly His Leu Val Leu Lys Trp Leu
    530                 535                 540

Ile Glu Gln Asp Thr Lys Met Lys Asp Thr Glu Arg Glu Glu Arg Phe
545                 550                 555                 560

Ser Arg Ile Leu Leu Glu Lys Val Gly Leu Glu Asn Leu Lys Thr Trp
                565                 570                 575

Ala Ser Val Asn Arg Gly Ala Ile Ile Leu Cys Cys Leu Leu Gln Ser
            580                 585                 590

Ala Asp Glu Ser Val Ala Glu Glu Val Lys Ala Met Leu Lys Ser Ser
        595                 600                 605

Ile Pro Glu Leu Gln Arg Leu Gln Asn Ser Lys Gly Ile Glu Val Leu
    610                 615                 620

Leu Glu Lys Leu Ala
625
```

<210> SEQ ID NO 3
<211> LENGTH: 2232
<212> TYPE: DNA
<213> ORGANISM: Homo sapiens

<400> SEQUENCE: 3

```
ggcccggggg cggagcaagg caaggaagcg gaagcggaga ggcggtcggg atccgctgcg      60

cgagctgtct cggtcccacg tgtgcgagtt gctacgatgg aagttaaagg gaaaaagcaa     120

ttcacaggaa agagtacaaa gacagcacaa gaaaaaaaca gatttcataa aaatagtgat     180

tctggttctt caaagacatt tccaacaagg aaagttgcta aagaaggtgg acctaaagtc     240

acatctagga actttgagaa aagtatcaca aaacttggga aaaagggtgt aaagcagttc     300

aagaataagc agcaagggga caaatcacca aagaacaaat tccagccggc aaataaattc     360

aacaagaaga gaaaattcca gccagatggt agaagcgatg aatcagcagc caagaagccc     420

aaatgggatg acttcaaaaa gaagaagaaa gaactgaagc aaagcagaca actcagtgat     480

aaaaccaact atgacattgt tgttcgggca aagcagatgt gggagatttt aagaagaaaa     540

gactgtgaca aagaaaaaag agtaaagtta atgagtgatt tgcagaagtt gattcaaggg     600

aaaattaaaa ctattgcatt tgcacacgat tcaactcgtg tgatccagtg ttacattcag     660

tatggtaatg aagaacagag aaaacaggct tttgaagaat tgcgagatga tttggttgag     720

ttaagtaaag ccaaatattc gagaaatatt gttaagaaat ttctcatgta tggaagtaaa     780

ccacagattg cagagataat cagaagtttt aaaggccacg tgaggaagat gctgcggcat     840

gcggaagcat cagccatcgt ggagtacgca tacaatgaca aagccatttt ggagcagagg     900
```

```
aacatgctga cggaagagct ctatgggaac acatttcagc tttacaagtc agcagatcac    960

cgaactctgg acaaagtgtt agaggtacag ccagaaaaat tagaacttat tatggatgaa   1020

atgaaacaga ttctaactcc aatggcccaa aaggaagctg tgattaagca ctcattggtg   1080

cataaagtat tcttggactt ttttacctat gcacccccca aactcagatc agaaatgatt   1140

gaagccatcc gcgaagcggt ggtctacctg gcacacacac acgatggcgc cagagtggcc   1200

atgcactgcc tgtggcatgg cacgcccaag gacaggaaag tgattgtgaa aacaatgaag   1260

acttatgttg aaaaggtggc taatggccaa tactcccatt tggttttact ggcggcattt   1320

gattgtattg atgatactaa gcttgtgaag cagataatca tatcagaaat tatcagttca   1380

ttgcctagca tagtaaatga caaatatgga aggaaggtcc tattgtactt actaagcccc   1440

agagatcctg cacatacagt acgagaaatc attgaagttc tgcaaaaagg agatggaaat   1500

gcacacagta agaaagatac agaggtccgc agacgggagc tcctagaatc catttctcca   1560

gctttgttaa gctacctgca agaacacgcc caagaagtgg tgctagataa gtctgcgtgt   1620

gtgttggtgt ctgacattct gggatctgcc actggagacg ttcagcctac catgaatgcc   1680

atcgccagct tggcagcaac aggactgcat cctggtggca aggacggaga gcttcacatt   1740

gcagaacatc ctgcaggaca tctagttctg aagtggttaa tagagcaaga taaaaagatg   1800

aaagaaaatg ggagagaagg ttgttttgca aaaacacttg tagagcatgt tggtatgaag   1860

aacctgaagt cctgggctag tgtaaatcga ggtgccatta ttctttctag cctcctccag   1920

agttgtgacc tggaagttgc aaacaaagtc aaagctgcac tgaaaagctt gattcctaca   1980

ttggaaaaaa ccaaaagcac cagcaaagga atagaaattc tacttgaaaa actgagcaca   2040

taggtggaaa gagttaagag caagatggaa tgattttttc tgttctctgt tctgtttccc   2100

aatgcagaaa agaaggggta gggtccacca tactggtaat tggggtactc tgtatatgtg   2160

tttcttcttt gtatacgaat ctatttatat aaattgtttt tttaaatggt ctttttttaaa   2220

aaaaaaaaaa aa                                                       2232
```

```
<210> SEQ ID NO 4
<211> LENGTH: 648
<212> TYPE: PRT
<213> ORGANISM: Homo sapiens

<400> SEQUENCE: 4

Met Glu Val Lys Gly Lys Lys Gln Phe Thr Gly Lys Ser Thr Lys Thr
1               5                   10                  15

Ala Gln Glu Lys Asn Arg Phe His Lys Asn Ser Asp Ser Gly Ser Ser
            20                  25                  30

Lys Thr Phe Pro Thr Arg Lys Val Ala Lys Glu Gly Gly Pro Lys Val
        35                  40                  45

Thr Ser Arg Asn Phe Glu Lys Ser Ile Thr Lys Leu Gly Lys Lys Gly
    50                  55                  60

Val Lys Gln Phe Lys Asn Lys Gln Gln Gly Asp Lys Ser Pro Lys Asn
65                  70                  75                  80

Lys Phe Gln Pro Ala Asn Lys Phe Asn Lys Lys Arg Lys Phe Gln Pro
                85                  90                  95

Asp Gly Arg Ser Asp Glu Ser Ala Ala Lys Lys Pro Lys Trp Asp Asp
            100                 105                 110

Phe Lys Lys Lys Lys Lys Glu Leu Lys Gln Ser Arg Gln Leu Ser Asp
        115                 120                 125
```

-continued

```
Lys Thr Asn Tyr Asp Ile Val Val Arg Ala Lys Gln Met Trp Glu Ile
    130                 135                 140

Leu Arg Arg Lys Asp Cys Asp Lys Glu Lys Arg Val Lys Leu Met Ser
145                 150                 155                 160

Asp Leu Gln Lys Leu Ile Gln Gly Lys Ile Lys Thr Ile Ala Phe Ala
                165                 170                 175

His Asp Ser Thr Arg Val Ile Gln Cys Tyr Ile Gln Tyr Gly Asn Glu
            180                 185                 190

Glu Gln Arg Lys Gln Ala Phe Glu Glu Leu Arg Asp Asp Leu Val Glu
        195                 200                 205

Leu Ser Lys Ala Lys Tyr Ser Arg Asn Ile Val Lys Lys Phe Leu Met
    210                 215                 220

Tyr Gly Ser Lys Pro Gln Ile Ala Glu Ile Ile Arg Ser Phe Lys Gly
225                 230                 235                 240

His Val Arg Lys Met Leu Arg His Ala Glu Ala Ser Ala Ile Val Glu
                245                 250                 255

Tyr Ala Tyr Asn Asp Lys Ala Ile Leu Glu Gln Arg Asn Met Leu Thr
            260                 265                 270

Glu Glu Leu Tyr Gly Asn Thr Phe Gln Leu Tyr Lys Ser Ala Asp His
        275                 280                 285

Arg Thr Leu Asp Lys Val Leu Glu Val Gln Pro Glu Lys Leu Glu Leu
    290                 295                 300

Ile Met Asp Glu Met Lys Gln Ile Leu Thr Pro Met Ala Gln Lys Glu
305                 310                 315                 320

Ala Val Ile Lys His Ser Leu Val His Lys Val Phe Leu Asp Phe Phe
                325                 330                 335

Thr Tyr Ala Pro Pro Lys Leu Arg Ser Glu Met Ile Glu Ala Ile Arg
            340                 345                 350

Glu Ala Val Val Tyr Leu Ala His Thr His Asp Gly Ala Arg Val Ala
        355                 360                 365

Met His Cys Leu Trp His Gly Thr Pro Lys Asp Arg Lys Val Ile Val
    370                 375                 380

Lys Thr Met Lys Thr Tyr Val Glu Lys Val Ala Asn Gly Gln Tyr Ser
385                 390                 395                 400

His Leu Val Leu Leu Ala Ala Phe Asp Cys Ile Asp Asp Thr Lys Leu
                405                 410                 415

Val Lys Gln Ile Ile Ile Ser Glu Ile Ile Ser Ser Leu Pro Ser Ile
            420                 425                 430

Val Asn Asp Lys Tyr Gly Arg Lys Val Leu Leu Tyr Leu Leu Ser Pro
        435                 440                 445

Arg Asp Pro Ala His Thr Val Arg Glu Ile Ile Glu Val Leu Gln Lys
    450                 455                 460

Gly Asp Gly Asn Ala His Ser Lys Lys Asp Thr Glu Val Arg Arg Arg
465                 470                 475                 480

Glu Leu Leu Glu Ser Ile Ser Pro Ala Leu Leu Ser Tyr Leu Gln Glu
                485                 490                 495

His Ala Gln Glu Val Val Leu Asp Lys Ser Ala Cys Val Leu Val Ser
            500                 505                 510

Asp Ile Leu Gly Ser Ala Thr Gly Asp Val Gln Pro Thr Met Asn Ala
        515                 520                 525

Ile Ala Ser Leu Ala Ala Thr Gly Leu His Pro Gly Gly Lys Asp Gly
    530                 535                 540
```

-continued

```
Glu Leu His Ile Ala Glu His Pro Ala Gly His Leu Val Leu Lys Trp
545                 550                 555                 560

Leu Ile Glu Gln Asp Lys Lys Met Lys Glu Asn Gly Arg Glu Gly Cys
                565                 570                 575

Phe Ala Lys Thr Leu Val Glu His Val Gly Met Lys Asn Leu Lys Ser
            580                 585                 590

Trp Ala Ser Val Asn Arg Gly Ala Ile Ile Leu Ser Ser Leu Leu Gln
        595                 600                 605

Ser Cys Asp Leu Glu Val Ala Asn Lys Val Lys Ala Ala Leu Lys Ser
    610                 615                 620

Leu Ile Pro Thr Leu Glu Lys Thr Lys Ser Thr Ser Lys Gly Ile Glu
625                 630                 635                 640

Ile Leu Leu Glu Lys Leu Ser Thr
                645
```